US009301968B2

(12) United States Patent
Kohno et al.

(10) Patent No.: US 9,301,968 B2
(45) Date of Patent: Apr. 5, 2016

(54) THERAPEUTIC AGENT FOR INFLAMMATORY DISEASES, CONTAINING ADENOSINE N1-OXIDE AS AN EFFECTIVE INGREDIENT

(71) Applicant: Hayashibara Co., Ltd., Okayama (JP)

(72) Inventors: Keizo Kohno, Okayama (JP); Emiko Ohashi, Okayama (JP); Hajime Kusano, Okayama (JP); Shigeharu Fukuda, Okayama (JP); Tatsuya Ishihara, Okayama (JP)

(73) Assignee: HAYASHIBARA CO., LTD., Okayama (JP)

( * ) Notice: Subject to any disclaimer, the term of this patent is extended or adjusted under 35 U.S.C. 154(b) by 0 days.

(21) Appl. No.: 14/323,091

(22) Filed: Jul. 3, 2014

(65) Prior Publication Data

US 2014/0315849 A1    Oct. 23, 2014

Related U.S. Application Data

(62) Division of application No. 13/805,215, filed as application No. PCT/JP2011/063804 on Jun. 16, 2011, now abandoned.

(30) Foreign Application Priority Data

Jun. 18, 2010   (JP) .................................. 2010-139969

(51) Int. Cl.
| | |
|---|---|
| A01N 43/04 | (2006.01) |
| A61K 31/70 | (2006.01) |
| A61K 31/708 | (2006.01) |
| A61K 45/06 | (2006.01) |
| A61K 31/7056 | (2006.01) |
| A61K 31/706 | (2006.01) |
| A61K 31/7064 | (2006.01) |
| A61K 31/7052 | (2006.01) |
| A61K 31/7076 | (2006.01) |
| C07H 19/167 | (2006.01) |
| C07H 19/067 | (2006.01) |

(52) U.S. Cl.
CPC ............ *A61K 31/708* (2013.01); *A61K 31/706* (2013.01); *A61K 31/7052* (2013.01); *A61K 31/7056* (2013.01); *A61K 31/7064* (2013.01); *A61K 31/7076* (2013.01); *A61K 45/06* (2013.01); *C07H 19/067* (2013.01); *C07H 19/167* (2013.01)

(58) Field of Classification Search
None
See application file for complete search history.

(56) References Cited

U.S. PATENT DOCUMENTS

| | | | |
|---|---|---|---|
| 4,088,756 A | 5/1978 | Voorhees | |
| 5,773,423 A | 6/1998 | Jacobson et al. | |
| 2003/0008841 A1 | 1/2003 | Devos et al. | |

FOREIGN PATENT DOCUMENTS

| | | |
|---|---|---|
| EP | 0066918 A1 | 12/1982 |
| JP | 58-41821 A | 3/1983 |
| JP | 5058812/97 A | 6/1997 |
| JP | 10-025251 A | 5/1998 |
| JP | 10130149 A | 5/1998 |
| WO | 9502604 A1 | 1/1995 |
| WO | 0211735 A2 | 2/2002 |
| WO | 03007974 A1 | 1/2003 |
| WO | 2006059328 A1 | 6/2006 |

OTHER PUBLICATIONS

Felder et al. The American Journal of Gastroenterology (2000), vol. 95, pp. 1949-1954.*
Hattori et al., AMP N1-oxide potentiates astrogenesis by cultured neural stem/progenitor cells through STAT3 activation, Biomedical Research, 28(6):295-299 (2007).
Supplementary European Search Report issued in corresponding European Patent Application No. EP11795806, mailed Jan. 14, 2014.
Tohru Noji, Akira Karasawa and Hideaki Kusaka, Pharmacological study on the effects of the adenosine uptake inhibitor KF24345 on inflammatory diseases, Folia Pharmacological Japonica, 2003, pp. 121-134, vol. 122, Pharmaceutical Research Institute, Japan.
Richard E. Klabunde, Dipyridamole Inhibition of Adenosine Metabolism in Human Blood, The European Journal of Pharmacology, 1983, pp. 21-26, vol. 93, Elsevier, Amsterdam.
Bazil, C. and Minneman, K., An Investigation of the Low Intrinsic Activity of Adenosine and Its Analogs at Low Affinity (A2) Adenosine Receptors in Rat Cerebral Cortex, fD1mwl of Neurochemistry, 1986, pp. 547-553, vol. 47. No. 2, Raven Press, United States.
Kane et al. Journal of Virology (1995), vol. 69, pp. 6352-6358.

* cited by examiner

*Primary Examiner* — Patrick Lewis
(74) *Attorney, Agent, or Firm* — Browdy and Neimark, PLLC

(57) ABSTRACT

The present invention has an object to provide an effective and safe therapeutic agent for inflammatory diseases such as sepsis, hepatitis, and inflammatory bowel disease, and solves the above object by providing a therapeutic agent for inflammatory diseases containing adenosine N1-oxide or a derivative thereof as an effective ingredient.

4 Claims, No Drawings

THERAPEUTIC AGENT FOR INFLAMMATORY DISEASES, CONTAINING ADENOSINE N1-OXIDE AS AN EFFECTIVE INGREDIENT

TECHNICAL FIELD

The present invention relates to an agent for treating inflammatory diseases such as sepsis and hepatitis, more particularly, to a therapeutic agent for inflammatory diseases, containing adenosine N1-oxide as an effective ingredient.

BACKGROUND ART

At present, there has not yet been explored a chemotherapeutic agent that exerts a satisfactory result for inflammatory diseases such as sepsis and hepatitis, and there have been only applied steroids, anti-inflammatories, platelet aggregation inhibitors, vasodilators, antibiotics, etc., as supportive measures to the above diseases. Since these inflammatory diseases exhibit serious symptoms in many cases, there has been desired an exploitation of therapeutically effective agents with no or lesser side-effects but with safeness.

It is known that many cytokines are involved in various inflammatory diseases in living bodies. Examples of such inflammatory cytokines include a number of tumor necrosis factor (TNF-$\alpha$), interleukins (ILs) such as IL-1, IL-6 and IL-12, and interferon (IFN)-$\gamma$, which have pharmacological actions other than their relation to inflammations. Among which, TNF-$\alpha$ was once discovered as a cytokine having an anti-tumor activity and it has been expected as an anti-cancer drug; however, after which it was revealed to be the same substance as cachectin, i.e., a cachexia-inducing factor. Further, TNF-$\alpha$ has an action of stimulating the production of other cytokines such as IL-1, etc., as well as actions of proliferating fibroblasts, inducing endotoxin shock, and inducing arthritis such as cartilage-destructing action; and it is suggested that inflammatory diseases have a causal correlation with the abnormal production of TNF-$\alpha$ (see, for example, Japanese Patent Laid-Open No. 25251/98, Japanese Unexamined Patent Application Publication No. 505812/97, Japanese Patent Laid-Open No. 130149/98, and International Patent Publication No. WO03/007974).

Among inflammatory diseases in which the abnormal production of TNF-$\alpha$ is deemed involved, for example, a serious one of resulting in a catastrophic outcome such as cardiac asystole/death after the condition of acute cardiovascular failure such as endotoxin shock induced by sepsis accompanied by bacterial infection. Further, TNF-$\alpha$ has been also suggested to be involved in the fulminant of rheumatoid arthritis (RA), acute respiratory distress syndrome (abbreviated as "ARDS", hereinafter), and autoimmune or viral hepatitis; and in the occurrence or the exacerbation of acute and serious clinical conditions such as inflammatory bowel disease.

Recently, as a therapeutic agent for inflammatory diseases to inhibit the abnormal production of TNF-$\alpha$, an anti-TNF-$\alpha$ antibody (see, for example, Japanese Patent Laid-Open No. 25251/98 and Japanese Unexamined Patent Application Publication No. 505812/97) and TNF-$\alpha$ production inhibitor (see, for example, Japanese Patent Laid-Open No. 130149/98 and International Patent Publication No. WO03/007974) have been tried to apply for the treatment of such inflammatory diseases; however, no satisfactory effect has not yet been attained thereby, and in some cases, a relatively long term administration thereof may cause side effects as a problem.

Also, adenosine as an endogenous purine nucleotide relates to the regulation of various biological reactions via the binding onto cell surface receptors. There exists a finding that adenosine has an anti-inflammatory action and an ischemic injury inhibitory action, however, it has relatively strong systemic side-effects. Furthermore, adenosine is promptly absorbed by hematocytes and vascular endothelial cells in the blood, metabolized and hydrolyzed to lose its action within a relatively short period of time. Because of this, clinical application thereof is limited. To compensate for the defect and to increase the concentration of adenosine at inflammatory sites, as well as to decrease the expression of the systemic side-effects, the exploitation of inhibitors for intracellular-intake of adenosine has been also under way (see, for example, "*Folia Pharmacological Japonica*", Vol. 122, pp. 121-134, 2003).

DISCLOSURE OF INVENTION

The present invention aims to provide an effective and safe therapeutic agent for inflammatory diseases.

To overcome the above object, the present inventors energetically studied and found that adenosine N1-oxide and derivatives thereof are useful as therapeutic agents for inflammatory diseases such as sepsis, hepatitis, and inflammatory bowel disease.

Further, the present inventors found that a therapeutic agent for inflammatory diseases containing adenosine N1-oxide or a derivative thereof as an effective ingredient has an action of inhibiting the production of inflammatory cytokines such as TNF-$\alpha$, IL-1, IL-4, IL-5, IL-6, IL-8 and IL-12, which have been considered as effector molecules for the onset or the exacerbation of inflammatory diseases; and that it has an action of enhancing the production of IL-10 as an anti-inflammatory cytokine that is recognized to contribute to the inhibition of inflammatory diseases. They also found that it can be used for the manufacture of a TNF-$\alpha$ production inhibitor, IL-1 production inhibitor, IL-4 production inhibitor, IL-5 production inhibitor, IL-6 production inhibitor, IL-8 production inhibitor, IL-12 production inhibitor, or IL-10 production enhancer for use in the treatment of inflammatory diseases. Thus, they accomplished the present invention.

The present invention solves the above object by providing a therapeutic agent for inflammatory diseases, which contains adenosine N1-oxide or a derivative thereof as an effective ingredient.

Further, the present invention solves the above object by providing a therapeutic agent for inflammatory diseases, which contains adenosine N1-oxide or a derivative thereof as an effective ingredient, usable for producing production inhibitors for TNF-$\alpha$, IL-1, IL-4, IL-5, IL-6, IL-8 or IL-12, as well as for producing production enhancers for IL-10.

In a preferred embodiment, the therapeutic agent, which contains adenosine N1-oxide or a derivative thereof as an effective ingredient, can be used in the fields of cosmetics, quasi-drugs, or pharmaceuticals in the form of an external dermal agent directed for use in improving skin inflammation such as dermatitis induced by physicochemical stimulation of chemical substances, ultraviolet rays, oxidant stress, and toxiods, or by microbial infections; allergic dermatitis; and atopic dermatitis; as well as for use in inhibiting or improving skin abnormality such as spots, pigmentation, occurrence of wrinkles, rough skin, and skin ageing, which could be induced by the above-mentioned inflammation.

The therapeutic agent, containing adenosine N1-oxide or a derivative thereof as an effective ingredient, effectively prevents or treats inflammatory diseases such as sepsis, rheumatoid arthritis, ARDS, hepatitis, and inflammatory bowel disease. In addition, the therapeutic agent of the present invention effectively inhibits the production of inflammatory cytokines such as TNF-α, IL-1, IL-4, IL-5, IL-6, IL-8, and IL-12. Further, the therapeutic agent effectively enhances the production of IL-10.

BEST MODE FOR CARRYING OUT THE INVENTION

The following concretely explain the therapeutic agent for inflammatory diseases of the present invention. The term "inflammatory diseases" as referred to as in the present invention means diseases which the onset or the exacerbation is correlated with inflammatory reaction, particularly, inflammatory diseases which are correlated with the abnormal production of inflammatory cytokines such as TNF-α and IL-6. Concretely speaking, examples of such are sepsis, rheumatoid arthritis, ARDS, hepatitis, inflammatory bowel disease, pancreatitis, arthritis, arterial sclerosis, ischemia-reperfusion injury, uveitis, endotoxin shock, burn injury, acute phase of viral myocarditis, idiopathic dilated cardiomyopathy, transition of organ failure from SIRS (systemic inflammatory response syndrome), multi organ failure, diseases inherent to endocapillary cell disorder including hemolytic-uremic syndrome or hemorrhagic colitis, hypergammaglobulinemia, systemic lupus erythematosus (SLE), multiple sclerosis, monoclonal B cell disorder, polyclonal B cell disorder, atrial myxoma, Castleman's disease, nephritis (such as primary glomerulonephritis, mesangial nephritis, and diabetic nephropathy), and skin inflammatory (such as postmenopausal osteoporosis, gingivitis, suntan, allergic dermatitis, and atopic dermatitis). Examples of the term "hepatitis" as referred to as in the present invention means alcoholic hepatitis, virus hepatitis, drug associated hepatitis, non-alcoholic fatty liver, autoimmune hepatitis, liver fibrosis, cirrhosis, and fulminant hepatitis, as well as diseases inherent to vascular endothelial inflammation such as cardiac infarct and brain infarct.

Further, examples of the inflammatory bowel diseases include ulcerative colitis and Crohn disease. The term "abnormal production of TNF-α" as referred to as in the present invention means that the concentration of TNF-α increases up to a level sufficient for inducing pyrexia, the onset or the exacerbation of inflammation, shock symptom, or organ failure in living bodies.

The therapeutic agent of the present invention contains adenosine N1-oxide (CAS No. 146-92-9) or a derivative thereof as an effective ingredient. These adenosine N1-oxides can be chemically synthesized ones, independently of their origins. The term "derivatives of adenosine N1-oxide" as referred to as in the present invention means substances, where at least one molecule of phosphoric acid or saccharide(s) such as glucose(s) bind(s) to the C-3 or C-5 of the ribose residue in adenosine N1-oxide molecule, which have substantially the same anti-inflammatory action as adenosine N1-oxide (may be called "adenosine N1-oxides", hereinafter). Concrete examples of such are α-glucosyl-adenosine N1-oxides, where one or two glucose molecules are bound to adenosine N1-oxide, such as 3'-α-glucosyl-adenosine N1-oxide and 5'-α-glucosyl-adenosine N1-oxide; and adenosine N1-oxide monophosphate such as adenosine N1-oxide 5'-monophosphate, adenosine N1-oxide diphosphate such as adenosine N1-oxide 5'-diphosphate, and adenosine N1-oxide triphosphate such as adenosine N1-oxide 5'-triphosphate, where one or more phosphoric acid molecules are bound to adenosine N1-oxide. In terms of the function and effect, preferable are adenosine N1-oxide, 3'-α-glucosyl-adenosine N1-oxide and adenosine N1-oxide 5'-monophosphate, particularly, adenosine N1-oxide and α-glucosyl-adenosine N1-oxide; and more particularly, adenosine N1-oxide. As α-glucosyl-adenosine N1-oxide, 3'-α-glucosyl-adenosine N1-oxide is more preferable than 5'-α-glucosyl-adenosine N1-oxide because the former has a stronger anti-inflammatory action than the latter. These compounds may contain ingredients originated from their production materials or by-products formed in their synthetic processes as long as they do not substantially affect on the safeness and the therapeutic effects on inflammatory diseases, as well as on the action of production inhibition for inflammatory cytokines such as TNF-α and IL-6. In the case of formulating vascularly administrable preparations, preferably used are those which have the highest possible purity, usually, those with a purity of 95% by weight or higher (throughout the specification "% by weight" is represented by "%", unless specified otherwise), on a dry solid basis (d.s.b.), more preferably, 98% by weight or higher, and most preferably, 99% by weight or higher. In the case of using for injection administration, particularly, vascular-injection, those which are substantially free of microorganisms and pyrogen can be used.

The therapeutic agent for inflammatory diseases can be provided in the form of an injection in general or a pharmaceutical preparation for oral use. In the case of preparing injections, liquids, emulsions, and suspensions, which contain any of adenosine N1-oxides as an effective ingredient, are sterilized and, preferably, they should substantially be free of pyrogen and isotonic to the blood. When forming into these forms, any of the following solvents conventionally used in the art can be used; refined water, physiological saline, phosphate buffered saline (PBS), and lactated Ringer's solution. In addition, ethyl alcohol, macrogol, propylene glycol, ethoxylated isostearyl alcohols, polyoxylated isostearyl alcohols, etc., can be used.

The therapeutic agent for inflammatory diseases in the form of an injection according to the present invention is usually provided in the form of a preparation into which at least one pharmaceutically acceptable additive(s) is/are incorporated along with any of adenosine N1-oxides as an effective ingredient. In the therapeutic agent for inflammatory diseases of the present invention, any additives usually used in the art can be appropriately used. Examples of such pharmaceutical additives include tonicity agents, buffers, pH-controlling agents, diluents, etc., which are usually used for injections in general.

Examples of the tonicity agents include saccharides and sugar alcohols such as glucose, maltose, α,α-trehalose, sorbitol, and mannitol; polyalcohols such as glycerin, propylene glycol, and polyethylene glycol; and electrolyte such as sodium chloride.

Examples of the buffers include citrate buffer, acetate buffer, phosphate buffer, and tartaric acid buffer.

Examples of the pH-controlling agents include those which are usually used in injections. Concretely speaking, for example, acid substances such as acetic acid, lactic acid, phosphoric acid, tartaric acid, citric acid, ascorbic acid, hydrochloric acid, gluconic acid, and sulfuric acid; and basic substances such as potassium hydroxide, sodium hydroxide, calcium hydroxide, magnesium hydroxide, monoethanolamine, diethanolamine, and triethanolamine. Amino acids such as glycine and histidine can be also used.

In addition to the above-mentioned agents, the following pharmaceutical ingredients effective for improving clinical symptoms of diseases, where TNF-α involves in the onset or the exacerbation thereof, can be incorporated; antimicrobials, vasodilators, antibiotics, non-steroidal anti-inflammatory drugs, steroidal anti-inflammatory drugs, vasopressors, inhibitors of blood coagulation, soothing agents, anti-TNF-α antibodies, adenine uptake inhibitors (see, for example, Non-Patent Literature 1), and vitamins.

The therapeutic agent for inflammatory diseases in the form of an injection can be prepared in usual manner. Concrete examples of such are as follows: Both adenosine N1-oxides as effective ingredients and additives are firstly dissolved in solvents free of pyrogen. The mixing order of these ingredients should not specifically be restricted, and all the components can be simultaneously mixed or mixed in such a manner of successively dissolving only a part of the total components and then dissolving the remaining components. Thereafter, the resulting solution is sterilized. The sterilization method used should not specifically be restricted, and usually methods such as filter sterilization, autoclaving, and heat sterilization can be used. The resulting sterilized agent can be, for example, injected and sealed in containers such as amples.

The therapeutic agent for inflammatory diseases of the present invention can be provided in the form of a solid preparation to be reconstituted upon use. Such preparation can be prepared in such a manner of drying the above injection preparation in the form of a liquid by conventional drying methods such as lyophilization and reduced-pressure drying to make into a powder or granule before injecting into containers such as amples and sealing them; and used for administration by dissolving the preparation in sterilized water, physiological saline, or infusion solution upon use into an aqueous solution, wherein the adenosine N1-oxides concentration is adjusted, for example, to give 0.1 to 10% as an adenosine N1-oxide concentration before administration.

When in the form of an injection, the therapeutic agent for inflammatory diseases of the present invention can be administered intravenously, intra-arterially, or intraperitoneally, intramuscularly, subcutaneously, or intradermally, depending on patients' syndromes; or administered intravenously after mixing with an infusion solution. The infusion solution to be mixed with the therapeutic agent for inflammatory diseases of the present invention is not specifically restricted, and any of commercially available infusion solutions can be used. Concrete examples of such are glucose injections, xylitol injections, D-mannitol injections, fructose injections, physiological saline, Ringer's solution, vitamin injections, amino acid injections, and electrolyte liquids. Depending on diseases or symptoms to be administered, the administration route of the therapeutic agent for inflammatory diseases of the present invention can be arbitrarily selected from ocular instillation, rhinenchysis, transnasal administration, and transpulmonary administration.

Further, as shown in the later Experiment, since the therapeutic agent for inflammatory diseases of the present invention can exert, when administered perorally, a similar effect on inflammatory diseases as in the case of being administered injectionally, it can be provided in the form of a perorally administrable pharmaceutical preparation in general. Such pharmaceutical preparation can be prepared by using fillers, bulking agents, binders, humectants, disintegrates, surfactants, lubricants, excipients/adjuvants, etc. The form of the above pharmaceutical preparation can be selected depending on its therapeutic purpose, and representative examples of such are tablets, balls, powders, liquids, suspensions, emulsions, granules, and capsules. When forming into a tablet, variety types of those which have been well known as carriers in the art can be generally used. Examples of such are, for example, saccharides such as lactose, white soft sugar, glucose, trehalose, and maltose; excipients/fillers/adjuvants such as starch, sodium chloride, urea, calcium carbonate, kaolin, crystalline cellulose, and hydrated silica; binders such as water, ethanol, propanol, gelatin solution, carboxymethyl cellulose, shellac, methyl cellulose, potassium phosphate, and polyvinylpyrrolidone; disintegrants such as dry starch, sodium alginate, powdered agar, powdered laminaran, sodium hydrogen carbonate, calcium carbonate, polyoxyethylene sorbitan fatty acid esters, sodium lauryl sulfate, stearyl monoglyceride, starch, and lactose; disintegration inhibitors such as white soft sugar, stearin, cacao butter, and hydrogenated oils; absorption accelerators such as quaternary ammonium base, and sodium lauryl sulfate; humectants such as glycerin and starch; adsorbents such as starch, lactose, kaolin, bentonite, and colloidal hydrated silica; and lubricants such as purified talc, stearate, boric acid powder, and polyethylene glycol. If necessary, the above-identified tablets can be formulated into those which are coated with conventional coating, such as sugar coated tablets, gelatin encapsulated tablets, enteric-coated tablets, film-coated tablets; or double coated tablets or multi-coated tablets. In the case of forming into balls, those which are conventionally known as carries in the art can be used. Concrete examples of such are saccharides such as glucose, lactose, trehalose, and maltose; excipients/fillers/adjuvants such as starch, cacao butter, hydrogenated vegetable oil, kaolin, and talc; binders such as powdered gum arabic, powdered tragacanth gum, pullulan, gelatin, and ethanol; and disintegrants such as laminaran and agar. In the case of forming into suppositories, those which are conventionally known as carries can be used. Examples of such are, for example, polyethylene glycols, higher alcohols, esters of higher alcohols, gelatin, and semisynthetic glycerides. The above-identified capsules can be prepared according to conventional manner of usually mixing the effective ingredient(s) and any of the above-exemplified carriers, and injecting the resulting mixture into a hard gelatin capsule or soft capsule. If necessary, coloring agents, preservatives, flavors, taste-imparting agents, sweeteners, and pharmaceutical ingredients similarly as in the case of the other injections can be arbitrarily incorporated into pharmaceutical preparations.

Further, the therapeutic agent for inflammatory diseases of the present invention can be provided in the form of a food product after incorporated into health supplements, etc. Such a food product can be prepared by using adenosine N1-oxides and foods or food additives. In such a case, the form thereof can be selected depending on its purpose, and representative examples of such are tablets, balls, powders, liquids, suspensions, emulsions, granules, and capsules. Further, the therapeutic agent for inflammatory diseases can be arbitrarily formed into those in the form of a sweet stuff/bread, processed food of cereal and meat, sweetener/seasoning, soft drink, alcoholic drink, or milk beverage in general.

The therapeutic agent for inflammatory diseases of the present invention can be provided after incorporated into external dermal agents such as cosmetics, quasi-drugs, and pharmaceuticals. Such external dermal agents can be usually incorporated into cosmetics, quasi-drugs, and base material ingredients for pharmaceutical external-dermal agents. Concretely speaking, for example, base material ingredients such as humectants, antioxidants, oily ingredients, ultraviolet-ray-absorbing agents, ultraviolet-ray-reflectance agents, surfactants, antiseptics, viscosity-imparting agents, buffers, pH-controlling agents, saccharides, sugar alcohols, powder constituents, colors, flavors, aqueous constituents, solvents such as water and alcohols, dermatological nutritional supplements, and plant/animal extracts can be appropriately incorporated into the therapeutic agent for inflammatory diseases of the present invention as required. As long as it can exert an anti-inflammatory effect on the skin, the form of the therapeutic agent for inflammatory diseases of the present invention used as an external dermal agent, which has been incorporated with any of the above base material ingredients, includes, for example, creams, ointments, emulsions, lotions, cosmetic lotions, jellies, mousses, packs, shampoos, rinses, hair-restorers, bath salts, tooth pastes, etc.

To exert the desired pharmaceutical effect, at least an effective amount of adenosine N1-oxides should naturally be incorporated into the therapeutic agent for inflammatory diseases of the present invention, and usually, in the case of injections, the content thereof is an amount of 0.01 to 10% in terms of adenosine N1-oxide, desirably, 0.1 to 2%. In the case of orally administrable agents, a recommended concentration is 1 to 90%, desirably, 10 to 90%. In the case of food products in the form of a tablet, ball, powder, liquid, suspension, emulsion, granule, and capsule, a preferable content is 1 to 90%, desirably, 10 to 90%. In the case of food products in general, a desirable content is 0.1 to 90%, more desirably, 1 to 10%. When incorporated into external dermal agents, a desirable content is 0.001 to 10%, more desirably, 0.01 to 1%.

Varying depending on patients' symptoms or ages to be intended, the dose of the therapeutic agent for inflammatory diseases of the present invention is usually 1 to 500 mg/day/kg body weight, more preferably, 10 to 300 mg/day/kg body weight in terms of adenosine N1-oxide, when administered via injection. When administered perorally, a recommended dose is 1 to 1,000 mg/day/kg body weight, preferably, 30 to 1,000 mg/day/kg body weight, more preferably, 100 to 800 mg/day/kg body weight in terms of adenosine N1-oxide. When prepared into the form of an external dermal agent, a recommended dose is 0.0005 to 5 mg/cm$^2$, preferably, 0.005 to 0.5 mg/cm$^2$ in terms of adenosine N1-oxide.

The therapeutic agent for inflammatory diseases of the present invention also includes pharmaceutical preparations in a dosage unit form. Examples of such means, for example, agents in a physically separable form suitable for administration, which contains a daily dose of the adenosine N1-oxides as effective ingredients of the present invention, a several times of the daily dose (up to four times), or an aliquot thereof (up to about ¼ time).

Since the therapeutic agent for inflammatory diseases containing adenosine N1-oxides of the present invention inhibits the production of inflammatory cytokines, which have an action of upregulating inflammatory reaction, for example, TNF-α, IL-1, IL-4, IL-5, IL-6, IL-8, IL-12, and IFN-γ, they can be used to treat inflammatory diseases as a production inhibitor for TNF-α, IL-1, IL-4, IL-5, IL-6, IL-8, IL-12, and IFN-γ. Since the therapeutic agent for inflammatory diseases of the present invention enhances the production of IL-10 which has an action of inhibiting inflammatory reaction, it can be used in treating inflammatory diseases as an agent for enhancing the production of IL-10. The therapeutic agent for inflammatory diseases of the present invention inhibits vascular endothelial cell damage, suppresses the expression on the cell surface of cell-adhesion factor and of tissue factor of vascular endothelial cell, and inhibits the formation of thrombus, it can be used to treat inflammatory diseases as an inhibitor of vascular endothelial cell damage, expression inhibitor of tissue factor, expression inhibitor of cell-adhesion factor, or formation inhibitor of thrombus.

Since the therapeutic agent for inflammatory diseases containing adenosine N1-oxides as effective ingredients of the present invention inhibits the production of TNF-α, IL-1, IL-4, IL-5, IL-6, IL-8, IL-12, and IFN-γ, which upregulate inflammatory reaction, and enhances the production of IL-10 which inhibits inflammatory reaction, it can be advantageously used as a therapeutic agent or an improving agent for inflammatory diseases and clinical symptoms accompanied thereby such as sepsis, hepatitis, and inflammatory bowel disease, as well as the following diseases which the above inflammatory cytokines are involved in their onsets or exacerbations; chronic rheumatoid arthritis, ARDS, pancreatitis, arthritis, arterial sclerosis, ischemia-reperfusion injury, uveitis, burn injury, acute phase of viral myocarditis, idiopathic dilated cardiomyopathy, DIC (disseminated intravascular coagulation), transition of organ failure from SIRS (systemic inflammatory response syndrome), multi organ failure, diseases inherent to endocapillary cell disorder inducing hemolytic-uremic syndrome or hemorrhagic colitis, hypergammaglobulinemia, systemic lupus erythematosus (SLE), multiple sclerosis, monoclonal B cell disorder, polyclonal B cell disorder, atrial myxoma, Castleman's disease, nephritis (primary glomerulonephritis, mesangial nephritis, and diabetic nephropathy), skin inflammation induced by physicochemical stimulation of chemical substances, ultraviolet rays, or oxidant stress, or by microbial infections; skin inflammation such as allergic dermatitis and atopic dermatitis; postmenopausal osteoporosis; diabetes; and periodontal disease. The therapeutic agent for inflammatory diseases of the present invention can be advantageously used for systemic chronic inflammatory reaction which is a basic clinical condition for the exacerbation of metabolic syndrome and the formation of diseases such as arterial sclerosis, myocardial infarction, and cerebral infarction, all of which are induced via the stimulation of pathogen sensors by an intrinsic ligand that is released by the tissues when they are damaged by the systemic mild inflammation observed in the adipose tissue and the vascular endothelium of patients with metabolic syndrome and potential patients thereof, as disclosed in "*Igaku-no-Ayumi*", Vol. 236, No. 4, pp. 243-248, 2011.

The therapeutic agent for inflammatory diseases of the present invention can be used for the purpose of ameliorating of or inhibiting the exacerbation of advancing inflammatory diseases, as well as a prophylactic agent for inhibiting the onset of inflammatory diseases.

The following Experiments explain the present invention.

Experiment 1

<Influence 1 of the Administration of Adenosine N1-Oxide on Bacterial Shock>

The influence of the administration of adenosine N1-oxide on sepsis was examined by using lipopolysaccharide (LPS)-induced endotoxin shock mice (see, for example, "*Circulation*", Vol. 111, pp. 97-105, 2005), which have been used widely as a model of bacterial shock accompanied by human sepsis. Fifteen BALB/c mice (9-week-old, female, commercialized by Charles River Laboratories Japan Inc., Tokyo, Japan) were randomly divided into three groups, five heads each (Experiment groups 1 to 3), and intraperitoneally administered with 15 mg/kg body weight of an LPS specimen derived from *Escherichia coli* (O55:B5), commercialized by Sigma-Aldrich Corporation, St. Louis, Mo. USA, which had been dissolved in phosphate buffered saline (PBS) (Experiment groups 1 to 3). Among these groups, five heads of one group were intravenously administered with 15 mg/kg body weight of adenosine N1-oxide (prepared by Hayashibara Biochemical Laboratories, Inc., Okayama, Japan, and may be abbreviated as "ANO", hereinafter), which had been dissolved in PBS, in a volume of 0.2 mL/head simultaneously with the administration of LPS (Experiment group 2). Another five heads of other one group were intravenously administered with 45 mg/kg body weight of adenosine N1-oxide, which had been dissolved in PBS, in a volume of 0.2 mL/head simultaneously with the administration of LPS (Experiment group 3). To the remaining five heads of another one group were intravenously administered with 0.2 mL/head of PBS simultaneously with the LPS administration (Experiment group 1). For each group, the survival number of mice was macroscopically observed up to 7 to 43 hours after the LPS administration, and based on this, the survival rate was determined for each group. The results are in Table 1. The survival rate (%) of mice for each group was calculated by dividing the survival number of mice at each observation time with the survival number of mice at the initiation of this experiment, and multiplying the obtained value by 100. For comparison, any of the adenosine N1-oxides used in the following Experiments were prepared by the following method at Hayashibara Biochemical Laboratories, Inc., Okayama, Japan.

<Preparation of Adenosine N1-Oxide>

Twenty grams of adenosine (commercialized by Sigma-Aldrich Corporation, St. Louis, Mo. USA, Product code: A9251-25G) was dispersed in one liter of acetic acid, admixed with 100 mL of hydrogen peroxide solution, and stirred at ambient temperature for five days. To the resulting solution was added five grams of 5% palladium on carbon, commercialized by Kawaken Fine Chemicals Co., Ltd, Tokyo, Japan, followed by decomposing an excessive amount of hydrogen peroxide, filtering the resultant to remove palladium carbon, drying the resulting solution in vacuo, adding ethanol to unstiffen the formed crystals, and filtering the resultant to obtain a crude crystalline adenosine N1-oxide. The crude crystals were dissolved by heating in two liters of ethanol, filtered, and ice chilled for crystallization, followed by repeating the recrystallization step twice to obtain eight grams of adenosine N1-oxide with a purity of 99.5%.

sidered to be directly attributed to a rapid progress of multiple organ failure. In this experiment, the fact that the time until the occurrence of individual death after having been induced bacterial shock by administering LPS was delayed by the administration of adenosine N1-oxide can be speculated that the progress of multiple organ failure was inhibited, and therefore the administration of adenosine N1-oxide can also effectively afford the time necessarily for exerting therapeutic effect on multiple organ failure by using conventional supportive measures used in treating sepsis.

Experiment 2

<Influence 1 of Adenosine N1-Oxide on the Production of TNF-α from Mouse Intraperitoneal Macrophage>

The confirmation of the fact that the administration of adenosine N1-oxide inhibits bacterial shock in mice administered with LPS in Experiment 1 led to examine the inhibitory mechanism of bacterial shock induced by adenosine N1-oxide in this experiment. It has been known that TNF-α induced by bacterial LPS is an effector molecule in bacterial shock in human sepsis (see, for example, "*Journal of Immunology*", Vol. 187, No. 3-5, pp. 346-356, 1993). The influence of adenosine N1-oxide on the production of TNF-α was examined by using mouse intraperitoneal macrophages known as an in vitro model of bacterial shock in human sepsis (see, for example, "*The Journal of Immunology*", Vol. 164, No. 9, pp. 1013-1019, 2000). It is known that mouse intraperitoneal macrophages respond to LPS to produce TNF-α whose production is more enhanced by the coexistence of IFN-γ. In bacterial shock, not only TNF-α but also other inflammatory cytokines such as IFN-γ would be produced, and therefore in this experiment, it is carried out in the coexistence of IFN-γ that is deemed to be close to clinical condi-

TABLE 1

| Experiment group | Dose of LPS (mg/kg body weight) | Dose of ANO (mg/kg body weight) | Number of mice (head) | Survival rate (%) of mice | | | |
|---|---|---|---|---|---|---|---|
| | | | | 7 Hours | 19 Hours | 26 Hours | 43 Hours |
| 1 | 15 | 0 | 5 | 100 | 80 | 60 | 40 |
| 2 | 15 | 15 | 5 | 100 | 100 | 80 | 80 |
| 3 | 15 | 45 | 5 | 100 | 100 | 100 | 80 |

ANO: Adenosine N1-oxide

As evident from Table 1, in the group (Experiment group 1), which had been administered with PBS simultaneously with the intraperitoneal administration of 15 mg/kg body weight of LPS, the survival rate was decreased with time after 19 hours after the administration and lowered to 40% at 43 hours after the administration. In contrast, compared to the group (Experiment group 1) which had been administered with PBS simultaneously with LPS, the group (Experiment group 2) and the group (Experiment group 3), which had been respectively administered with 15 mg/kg body weight or 45 mg/kg body weight of adenosine N1-oxide simultaneously with 15 mg/kg body weight of LPS, were observed to have been inhibited the decrease of their survival rates, depending on the dose of adenosine N1-oxide. This results reveal that adenosine N1-oxide is useful as a prophylactic or therapeutic agent for sepsis that effectively inhibits bacterial shock in sepsis. For comparison, in this experiment system, it was found a delayed time until the occurrence of individual death after having been induced bacterial shock by administering LPS, depending on the dose of adenosine N1-oxide. In the case of sepsis, the death induced by bacterial shock is contion of bacterial shock. Adenosine N1-oxide was dissolved in PBS for use because it has a higher water solubility than adenosine.

According to conventional manner, BALB/c mice, 7- to 10-week-old, female, commercialized by Japan Charles River, Tokyo, Japan, were intraperitoneally administered with two milliliters of 4% thioglycolate medium, and on three days after the administration, their intraperitoneals were washed with five milliliters of RPMI 1640 medium ("RPMI-1640 Medium", a product name of Sigma-Aldrich Co. LLC, USA) supplemented with 10% v/v FCS (called "RPMI 1640 medium supplemented with 10% FCS", hereinafter), and this washing step was repeated four times to collect peritoneal exudate cells. The cells thus obtained were washed twice with RPMI 1640 medium supplemented with 10% FCS and suspended in a fresh preparation of the same medium. The resulting cell suspension was added to a dish for tissue culture (product code: 353003, commercialized by Becton Drive Franklin Lakes, N.J., USA), and incubated in a 5% v/v $CO_2$ incubator at 37° C. for 1.5 hours to attach the peritoneal exudate macrophages on the surface of the dish. The resulting culture was removed from the dish which was then washed twice with RPMI 1640 medium supplemented with 10% FCS to remove unattached cells, followed by collecting the cells attached to the dish with a cell scraper. The collected cells were washed with RPMI 1640 medium supplemented with 10% FCS, and suspended in RPMI 1640 medium supplemented with 10% FCS and 50 μM mercaptoethanol to prepare mouse intraperitoneal macrophages. The resulting mouse intraperitoneal macrophages were suspended in RPMI 1640 medium supplemented with 10% FCS to give a cell concentration of $1 \times 10^6$ cells/mL, and inoculated to a 96-well microplate ("96-Well Microplate For Tissue Culture 353075", a product name of Becton, Dickinson and Company, CA, USA) in an amount of $5 \times 10^4$ cells/50 μL/well. In the presence of 2 μg/mL of LPS and 10 IU/mL of mouse IFN-γ, the cells were continued culturing for one day after adding thereto 50 μL/well of adenosine N1-oxide, which had been diluted with PBS to give respective final concentrations as shown in Table 2, followed by collecting each supernatant.

TNF-α in each collected supernatant was assayed with enzyme-linked immunosorbent assay (ELISA) (Experiment groups 2 to 5). As a control, in the presence of LPS and mouse IFN-γ, only RPMI 1640 medium supplemented with 10% FCS was added to the plate in an amount of 50 μL/well and the cells were continued culturing for two days, followed by collecting the supernatant in each well and assaying the level of TNF-α similarly as above (Experiment group 1). The viable cells in each well were measured on AlamarBlue method, and the cell viabilities were determined by calculating the relative values when the cell viability of the control was regarded as 100%. The results are in Table 2 in parallel. The test for each Experiment group was conducted by using three wells. The assay for TNF-α was conducted on an ELISA using a commercialized rat anti-mouse TNF-α antibody ("Rat anti-mouse/rat TNF antibody" (product code: 551225), a product name of Becton Drive Franklin Lakes, N.J., USA) as a solid phase antibody; a commercialized biotin-labeled rat anti-mouse TNF-α antibody ("Biotin-Labeled Rat Anti-Mouse TNF Antibody", product code: 554415, commercialized by Becton Drive Franklin Lakes, N.J., USA) as a secondary antibody; and an HRPO-labeled streptavidin.

TABLE 2

| Experiment group | LPS Concentration (μg/mL) | IFN-γ Concentration (IU/mL) | ANO Concentration (μM) | TNF-α Concentration (pg/mL) | Cell viability (%) |
|---|---|---|---|---|---|
| 1 | 2 | 10 | 0 | 1625 | 100 |
| 2 | 2 | 10 | 0.006 | 1573 | 100 |
| 3 | 2 | 10 | 0.031 | 1637 | 100 |
| 4 | 2 | 10 | 0.063 | 1136 | 100 |
| 5 | 2 | 10 | 0.313 | 545 | 100 |

ANO: Adenosine N1-oxide

As evident from Table 2, mouse intraperitoneal macrophages, which had been cultured with only RPMI 1640 medium supplemented with 10% FCS in the presence of LPS and IFN-γ, induced the production of TNF-α (Experiment group 1). On the contrary, in the case of culturing with adenosine N1-oxide in the presence of LPS and IFN-γ (Experiment groups 2 to 5), the production of TNF-α was significantly inhibited by adenosine N1-oxide depending on its concentration in the range of 0.063 μM or higher (Experiment groups 4 and 5). No influence of adenosine N1-oxide on cell viability was observed at the concentrations used in this experiment.

Experiment 3

<Influence 2 of Adenosine N1-Oxide on the Production of TNF-α and IL-6 from Mouse Intraperitoneal Macrophages>

Macrophages have been known to use a receptor called "Toll Like Receptor" (may be called "TLR", hereinafter) to recognize adventive pathogenic microorganisms, while LPS has been known to be recognized by a receptor called TLR4. It was confirmed that, in Experiment 2, the production of TNF-α from mouse intraperitoneal macrophages, induced by the stimulation of LPS derived from a gram negative microorganism and identified as a causative substance of bacterial shock, is effectively inhibited by adenosine N1-oxide. In this experiment, it was examined the influence of adenosine N1-oxide on the production of TNF-α from mouse intraperitoneal macrophages induced by the stimulation of a component derived from a microorganism, which has been recognized as a causative of inflammatory diseases and which is recognized by a receptor other than TLR4 and is derived from the one excluding a gram-negative microorganism. In place of the LPS used to stimulate macrophages in Experiment 2, except for using Pam3CSK4 ((Palmitoyl-Cys((RS)-2,3-di (palmitoyloxy)-propyl)-Ser-Lys-Lys-Lys-OH), a lipoprotein derived from gram-positive microorganism recognized by TLR1/2, commercialized Bachem Bioscience Inc, Philadelphia, USA, in a final concentration of 2.5 μg/mL; "Zymosan A", a yeast cell membrane component recognized by TLR2 commercialized by Sigma-Aldrich Corporation, St. Louis, Mo. USA in a final concentration of 100 μg/mL; Poly I:C which is frequently used as a substituent for a viral component that is recognized by TLR3, commercialized by Calbiochem-NoVabiochem Co., Ltd., San Diego, Calif., USA, in a final concentration of 50 μg/mL; and verotoxin I, which induces the production of an inflammatory cytokine that is taken into cells via the bonding of cell surface globotriosyl ceramide (Gb3; globotriosyl ceramide), a hemorrhagic-colitis-inducing causative produced from an enterohemorrhagic *Escherichia coli* or *Bacillus dysenteriae*, to stimulate macrophages; macrophages were cultured in a 5% v/v $CO_2$ incubator at 37° C. for 24 hours, and the resulting supernatant was subjected to an assay for IL-6 with ELISA. In addition, IL-6 was assayed with an ELISA using a commercialized rat anti-mouse IL-6 antibody ("Rat anti-mouse IL-6 antibody", a product code: 554400, commercialized by BD Pharmingen Inc., San Diego, Calif., USA, used as a solid phase, and a commercialized biotin-labeled rat anti-mouse IL-6 antibody ("Biotin-Labeled Rat Anti-Mouse IL-6 Antibody", produce code: 554402), commercialized by BD Pharmingen Inc., San Diego, Calif., USA, as a secondary antibody; and an HRPO-labeled Streptavidin. The results are in Table 3.

TABLE 3

| | Stimulation factor of macrophage | | | | | | | |
|---|---|---|---|---|---|---|---|---|
| Experiment group | ANO Concentration (μM) | LPS Concentration (μg/mL) | Pam3CSK4 Concentration (μg/mL) | Zymosan A concentration (μg/mL) | Poly I:C concentration (μg/mL) | Verotoxin I concentration (ng/mL) | TNF-α Concentration (pg/mL) | IL-6 Concentration (pg/mL) |
| 1 | 0 | 2 | 0 | 0 | 0 | 0 | 1211 | 5,732 |
| 2 | 0.2 | 2 | 0 | 0 | 0 | 0 | 680** | 5,816 |
| 3 | 0.5 | 2 | 0 | 0 | 0 | 0 | 534** | 4899** |
| 4 | 1 | 2 | 0 | 0 | 0 | 0 | 207** | 3685** |

TABLE 3-continued

| Experiment group | ANO Concentration (μM) | LPS Concentration (μg/mL) | Pam3CSK4 Concentration (μg/mL) | Zymosan A concentration (μg/mL) | Poly I:C concentration (μg/mL) | Verotoxin I concentration (ng/mL) | TNF-α Concentration (pg/mL) | IL-6 Concentration (pg/mL) |
|---|---|---|---|---|---|---|---|---|
| | | | | Stimulation factor of macrophage | | | | |
| 5 | 0 | 0 | 2.5 | 0 | 0 | 0 | 0 | 468 |
| 6 | 0.2 | 0 | 2.5 | 0 | 0 | 0 | 0 | 415 |
| 7 | 0.5 | 0 | 2.5 | 0 | 0 | 0 | 0 | 326** |
| 8 | 1 | 0 | 2.5 | 0 | 0 | 0 | 0 | 232** |
| 9 | 0 | 0 | 0 | 100 | 0 | 0 | 0 | 311 |
| 10 | 0.2 | 0 | 0 | 100 | 0 | 0 | 0 | 309 |
| 11 | 0.5 | 0 | 0 | 100 | 0 | 0 | 0 | 212** |
| 12 | 1 | 0 | 0 | 100 | 0 | 0 | 0 | 148** |
| 13 | 0 | 0 | 0 | 0 | 50 | 0 | 0 | 3,361 |
| 14 | 0.2 | 0 | 0 | 0 | 50 | 0 | 0 | 3,236 |
| 15 | 0.5 | 0 | 0 | 0 | 50 | 0 | 0 | 2,939 |
| 16 | 1 | 0 | 0 | 0 | 50 | 0 | 0 | 2,355** |
| 17 | 0 | 0 | 0 | 0 | 0 | 100 | 725 | 5,732 |
| 18 | 0.2 | 0 | 0 | 0 | 0 | 100 | 331** | 3,218 |
| 19 | 0.5 | 0 | 0 | 0 | 0 | 100 | 243** | 2310** |
| 20 | 1 | 0 | 0 | 0 | 0 | 100 | 99** | 1329** |

ANO: Adenosine N1-oxide
Pam3CSK4: Palmitoyl-Cys((RS)-2,3-di(palmitoryloxy)-propyl)-Ser-Lys-Lys-OH
*There exists a significant difference (p < 0.01) compared to the case with no addition of ANO to a group with the addition of macrophage stimulating factor.

As evident from Table 3, compared to the macrophages, which had been stimulated with LPS in the absence of adenosine N1-oxide, those which had been stimulated with LPS in the presence of 0.5 or 1 μM adenosine N1-oxide were inhibited in the production of IL-6 and TNF-α. The macrophages, which had been stimulated with Pam3CSK4, Zymosan A, or poly I:C in the presence of 0.5 or 1 μM adenosine N1-oxide, were inhibited in the production of IL-6 compared to those which had been stimulated with respective stimulants in the absence of adenosine N1-oxide, similarly as those stimulated with LPS. When stimulated with Zymosan A, macrophages tended to be inhibited in the production of IL-6 even at the concentration of 0.2 μM of adenosine N1-oxide. When stimulated with these substances, no production of TNF-α from macrophages was observed. Similarly as the macrophages stimulated with LPS, those which had been stimulated with verotoxin I in the presence of 0.5 or 1 μM adenosine N1-oxide were inhibited in the production of IL-6 and TNF-α compared to those stimulated with verotoxin I in the absence of adenosine N1-oxide. The production of TNF-α was inhibited even under the coexistence of 0.2 μM of adenosine N1-oxide. The results indicate that, since adenosine N1-oxide inhibits not only the production of IL-6 and TNF-α from macrophages via TLR4 receptor such as the stimulation of LPS derived from gram-negative bacteria but also the production of IL-6 and TNF-α from macrophages via other receptors other than TLR4, it can be useful as a therapeutic or prophylactic agent for inflammatory diseases induced via a receptor other than TLR4 inherent to the infection of pathogenic microorganisms such as gram-positive bacteria, yeasts, and viruses. It also indicates that adenosine N1-oxide is useful as a therapeutic and prophylactic agent for inflammatory diseases such as hemolytic-uremic syndrome and hemorrhagic colitis.

Experiment 4

<Influence of the Addition of Adenosine N1-Oxide and Adenosine on the Production of TNF-α from Mouse Macrophage-Like Cell Strain>

Similarly as in mouse intraperitoneal macrophages, the influence of adenosine N1-oxide on the production of TFN-α was examined by using "RAW264.7", a cell name of mouse macrophage-like cell strain (called "RAW264.7 cells", hereinafter), commercialized by Dainippon Sumitomo Pharma Co., Ltd., Tokyo, Japan, as an endotoxin shock in vitro model for human sepsis. Since adenosine N1-oxide would be metabolized into inosine via adenosine or metabolized via adenosine phosphate, the influence of adenosine on the TNF-α production in RAW264.7 cells was also examined. It is well known that inflammatory cytokines of IL-6 and IL-12 other than TNF-α relate to the onset of bacterial shock, the influence of adenosine N1-oxide on the production of IL-6 was also examined in this experiment. RAW264.7 cells were subjected to passage culture with RPMI 1640 medium supplanted with 10% FCS ("RPMI 1640 Medium", a product name of Sigma-Aldrich Corporation, St. Louis, Mo. USA) for use in test. RAW264.7 cells were collected from the resulting culture, suspended in RPMI 1640 medium supplemented with 10% FCS at a cell density of $1 \times 10^6$ cells/mL, inoculated to "96-Well Microplate for Tissue Culture", a product name of 96-well microplate commercialized by Becton, Dickinson and Company CA, USA, at a cell concentration of $5 \times 10^4$ cells/50 μL/well. To each well of the microplates were added adenosine N1-oxide which had been diluted with PBS to give the final concentrations shown in Table 3, followed by culturing the cells for one day and collecting the supernatants.

TNF-α in the collected each supernatant was assayed with ELISA (Experiment groups 2 to 8). In parallel, IL-6 in the each supernatant was assayed. After the addition of adenosine in place of adenosine N1-oxide to give the concentrations shown in Table 4, RAW264.7 cells were cultured, followed by assaying TNF-α and IL-6 (Experiment groups 9 to 15). As a control, a culture with only addition of RPMI 1640 medium supplemented with 10% FCS was conducted in the presence of LPS (Experiment group 1), followed by quantifying TNF-α and IL-6 in the supernatant. The viable cells in each well were measured with AlamarBlue method and expressed with a relative value for use as a cell viability (%), when the viable cells of the control was regarded as 100(%). These results are in Table 4 in parallel. For assaying TNF-α, the same method as in Experiment 2 was used. Also, for assaying IL-6, the same method as in Experiment 3 was used.

TABLE 4

| Experiment group | LPS Concentration (μg/mL) | ANO Concentration (μM) | AN Concentration (μM) | TNF-α Concentration (pg/mL) | IL-6 Concentration (pg/mL) | Cell viability (%) |
|---|---|---|---|---|---|---|
| 1 | 2 | 0 | 0 | 682.2 | 3250 | 100 |
| 2 | 2 | 0.1 | 0 | 648.7 | 3156 | 100 |
| 3 | 2 | 0.3 | 0 | 543.3 | 2993 | 100 |
| 4 | 2 | 0.6 | 0 | 361.6* | 2688* | 100 |
| 5 | 2 | 1 | 0 | 333.2* | 2645* | 100 |
| 6 | 2 | 3 | 0 | 259.1* | 2088* | 100 |
| 7 | 2 | 6 | 0 | 270.4* | 1739* | 100 |
| 8 | 2 | 12 | 0 | 162.3* | 1103* | 100 |
| 9 | 2 | 0 | 1 | 634.1 | 3062 | 100 |
| 10 | 2 | 0 | 3 | 460.2 | 2862 | 100 |
| 11 | 2 | 0 | 6 | 398.7 | 2768 | 100 |
| 12 | 2 | 0 | 12 | 404.5 | 2672* | 100 |
| 13 | 2 | 0 | 24 | 346.8* | 2624* | 99 |
| 14 | 2 | 0 | 32 | 308.5* | 2867* | 98 |
| 15 | 2 | 0 | 40 | 193.1* | 2435* | 97 |

ANO: Adenosine N1-oxide
AN: Adenosine
There exists a significant difference against Experiment group 1
(*P < 0.05,
**P < 0.01).

As evident from Table 4, RAW264.7 cells, which had been cultured in the presence of LPS, were observed to have produced TNF-α and IL-6 (a control, Experiment group 1). While, when cultured after adding LPS along with adenosine N1-oxide, the production inhibition of TNF-α and IL-6 was observed depending on the concentration of adenosine N1-oxide (Experiment groups 2 to 8). When adenosine was added in combination with LPS, the production inhibition of TNF-α and IL-6 was found depending on the concentration of adenosine (Experiment groups 9 to 15), although the level was lower than that with adenosine N1-oxide. Based on the measured values in Table 4, the concentration of adenosine N1-oxide or adenosine required for attaining 50% inhibition ($IC_{50}$) of the TNF-α concentration in a control was determined, revealing that they were 1.2 μM for adenosine N1-oxide and 22 μM for adenosine. Under the concentration used in the test, no reduction of cell survival rate of RAW264.7 cells was observed by the addition of adenosine N1-oxide. In the case of adding adenosine, cell survival rate was lowered in a dose-dependent manner.

The results in Experiments 2 to 4 suggest that one of the inhibitory mechanisms of bacterial shock by the addition of adenosine N1-oxide observed in Experiment 1 was the inhibition of the production of TNF-α, an inflammatory cytokine, from macrophages. Further, they also suggest that the inhibitory action of the production of IL-6 relates to the inhibition of bacterial shock by adenosine N1-oxide. These results indicate that adenosine N1-oxide is useful as an inhibitor for the production of TNF-α and IL-6 from macrophages induced by LPS. For comparison, comparing the above $IC_{50}$, it is concluded that adenosine N1-oxide has a stronger inhibitory action on the production of TNF-α and IL-6 than adenosine by several times.

Experiment 5

<Analysis of the Inhibitory Mechanism of the Production of TNF-α from Macrophage System Cells by Adenosine N1-Oxide>

Since Experiments 2 to 4 have revealed that adenosine N1-oxide inhibits the production of TNF-α and IL-6 from macrophages induced by LPS, the reactivity of adenosine N1-oxide with adenosine receptors $A_1R$, $A_{2A}R$, $A_{2B}R$, and $A_3R$ was examined in this experiment to examine in more detail the inhibitory mechanism of the production of TNF-α from macrophage system cells by adenosine N1-oxide. THP-1 Cells, a human monocytic cell strain (possessed by Hayashibara Biochemical Laboratories, Inc., Okayama, Japan), were suspended in RPMI 1640 medium supplemented with 10% FCS at a cell concentration of $1 \times 10^6$ cells/mL, and inoculated to "96-Well Microplate for Tissue Culture", a 96-well microplate commercialized by Becton, Dickinson and Company, CA, USA, in an amount of $1 \times 10^5$ cells/100 μL/well. Thereafter, any of DPCPX, an adenosine antagonist, commercialized by Sigma-Aldrich Corporation, St. Louis, Mo. USA; ZM241385, commercialized by Tocris Bioscience, MSY USA; MRS1754, commercialized by Sigma-Aldrich Corporation, St. Louis, Mo. USA; and MRS1220, commercialized by Tocris Bioscience, MSY USA were diluted with RPMI 1640 medium supplemented with 10% FCS to give the concentrations in Table 5, and added to the microplate in a volume of 50 μL/well, followed by incubating the cells at 37° C. for 30 min in a 5% v/v $CO_2$ incubator. Adenosine N1-oxide, which had been diluted with PBS to give the final concentrations as shown in Table 5, was added to the microplate in a volume of 50 μL/well, followed by adding to each well LPS (25 μg/mL) and human IFN-γ (500 IU/mL) in a volume of 100 μL/well, culturing the cells at 37° C. for 20 hours in a 5% v/v $CO_2$ incubator, and collecting the supernatant from each well for assaying TNF-α with ELISA. The results are in Table 5 in parallel. DPCPX is a specific antagonist against adenosine receptor $A_1R$ and is a compound represented by 8-cyclopentyl-1,3-dipropylxanthine. ZM241385 is a specific antagonist against adenosine receptor $A_{2A}R$ and is a compound represented by 4-(2-[7-amino-2-(2-furyl)[1,2,4]triazolo-[2,3-a][1,3,5]-triazin-5-ylamino]ethyl) phenol. MRS1754 is a specific antagonist against adenosine receptor $A_{2B}R$ and is a compound represented by 8-[4-[((4-cyanophenyl)carbamylethyl)-oyl]phenyl]-1,3-di(n-propyl) xanthine. MRS1220 is a specific antagonist against adenosine receptor $A_3R$ and a compound represented by N-[9-chloro-2-(2-furanyl)[1,2,4]triazolo-[1,5-c]quinazolin-5-yl]benzene.

TABLE 5

| Experiment group | ANO Concentration (μM) | DPCPX Concentration (μM) | ZM241385 Concentration (μM) | MRS1754 Concentration (μM) | MRS1220 Concentration (μM) | TNF-α Concentration (pg/mL) |
|---|---|---|---|---|---|---|
| 1 | 0 | 0 | 0 | 0 | 0 | 144 |
| 2 | 5 | 0 | 0 | 0 | 0 | 97 |
| 3 | 5 | 0.5 | 0 | 0 | 0 | 132** |
| 4 | 5 | 1 | 0 | 0 | 0 | 130** |
| 5 | 5 | 5 | 0 | 0 | 0 | 129** |
| 6 | 5 | 10 | 0 | 0 | 0 | 133** |
| 7 | 5 | 0 | 0.5 | 0 | 0 | 135** |
| 8 | 5 | 0 | 1 | 0 | 0 | 137** |
| 9 | 5 | 0 | 5 | 0 | 0 | 135** |

TABLE 5-continued

| Experiment group | ANO Concentration (μM) | DPCPX Concentration (μM) | ZM241385 Concentration (μM) | MRS1754 Concentration (μM) | MRS1220 Concentration (μM) | TNF-α Concentration (pg/mL) |
|---|---|---|---|---|---|---|
| 10 | 5 | 0 | 10 | 0 | 0 | 132** |
| 11 | 5 | 0 | 0 | 0.5 | 0 | 118** |
| 12 | 5 | 0 | 0 | 1 | 0 | 121** |
| 13 | 5 | 0 | 0 | 5 | 0 | 121** |
| 14 | 5 | 0 | 0 | 10 | 0 | 103* |
| 15 | 5 | 0 | 0 | 0 | 0.5 | 105** |
| 16 | 5 | 0 | 0 | 0 | 1 | 105** |
| 17 | 5 | 0 | 0 | 0 | 5 | 105** |
| 18 | 5 | 0 | 0 | 0 | 10 | 102** |

ANO: Adenosine N1-oxide.
There exists a significant difference against Experiment group 2
(*P < 0.05,
**P < 0.01).

As evident from Table 5, TNF-α produced by THP-1 cells in the coexistence of LPS and human IFN-γ (Experiment group 1) was significantly inhibited by the addition of adenosine N1-oxide (Experiment group 2). The production inhibition of TNF-α by the addition of adenosine N1-oxide was almost completely recovered when the cells were pretreated with DPCX, a specific antagonists against adenosine receptor $A_1R$; ZM241385, a specific antagonist against adenosine receptor $A_{2A}R$; and MRS1754, a specific antagonist against adenosine receptor $A_{2B}R$ (Experiment groups 3 to 14). When pretreated with MRS1220 as a specific antagonist against adenosine receptor $A_3R$, no recovery of the inhibition of TNF-α production by the addition of adenosine N1-oxide was observed. Under the conditions in this experiment, no influence was observed in the proliferation of THP-1 cells (Experiment groups 15 to 18). These results indicate that a signal transduction system via PKA (cAMP dependent protein kinase) relates to the production inhibition of TNF-α by adenosine N1-oxide. The existence of four types of $A_1R$, $A_{2A}R$, $A_{2B}R$, and $A_3R$ as adenosine receptors was confirmed based on the degree of affinity against adenosine and on the action of increasing and decreasing intracellular cyclic AMP, and it is also known that $A_{2A}R$ and $A_{2B}R$ mainly relate to and $A_3R$ may relate to the anti-inflammatory action by adenosine. Although a monophosphate compound of andesine N1-oxide act on cells by a signal transduction system via $A_{2A}R$ (see, for example, "Evid. Based Complement Alternat Med.", pp. 1-6, 2007), it can be concluded that the same signal transduction system as in adenosine relates to the production inhibition of TNF-α by adenosine N1-oxide according to the present invention. No involvement of adenosine receptor $A_3R$ in the anti-inflammatory action by adenosine N1-oxide was observed by the MRS1220 used in this experiment. Although concrete data is not shown, since adenosine receptor $A_3R$ relates to the proliferation inhibitory action of adenosine N1-oxide against human normal keratinocyte (NHEK cells) was observed in another experiment, adenosine $A_3R$ may possibly relate to the expression of anti-inflammatory action of adenosine N1-oxide.

Experiment 6

<Influence 2 of the Addition of Adenosine N1-Oxide and Adenosine on the Inflammatory Reaction of Human Vascular Endothelial Cells>

The influence of the addition of adenosine N1-oxide and adenosine on the TNF-α production was examined by using, as an in vitro model for endotoxin shock in human sepsis, human umbilical vein endothelial cells (called "HUVEC cells", hereinafter), commercialized by Kurabo Industries Ltd., Osaka, Japan, which had been known to induce the TNF-α production when cultured by the addition of LPS in the presence of IL-1β and IFN-γ, in place of the mouse RAW264.7 cells used in Experiment 4. It was also examined the influence of the addition of adenosine N1-oxide and adenosine on the expression of tissue factor and vascular cell adhesion molecule (VCAM-1), which relate to the formation of thrombus that has been deemed as a factor of exacerbation of symptoms in inflammatory reaction. HUVEC Cells, which had been cultured by using a culture flask with 75 cm², commercialized by CORNING Inc., NY, USA, coated with atelocollagen (product code: IPC-50), commercialized by Koken Co., Ltd., Tokyo, Japan, were detached from the culture flask with 0.05% trypsin/EDTA, commercialized by GIBCO Co, CA, USA, washed thrice with RPMI 1640 medium supplemented with 10% FCS, suspended with "HuMedia-EG2 medium" (product No.: KE-21505), a product name of a medium for proliferating vascular endothelial cells, commercialized by Kurabo Industries Ltd., Osaka, Japan, to give a cell concentration of $4 \times 10^4$ cells/mL, inoculated to "Gelatin-Coated Microplate 96-Well with a Lid", a 96-well multi-plate coated with gelatin commercialized by Iwaki Scitech, Tokyo, Japan, in an amount of 200 μL/well, and cultured at 37° C. in a 5% v/v $CO_2$ incubator until reaching confluent conditions for use in the following experiment.

Experiment 6-1

Influence on the Production of TNF-α and IL-6

To confluent HUVEC cells were added an adenosine or adenosine N1-oxide solution, prepared by dissolving adenosine (a reagent-grade specimen commercialized by Wako Pure Chemical Industries Ltd., Tokyo, Japan) or adenosine N1-oxide in a medium for proliferating vascular endothelial cells to give respective concentrations shown in Table 6, and a solution with a final concentration of 10 μg/mL for LPS, 2 ng/mL for human IL-1β, and 500 IU/mL for human IFN-γ prepared by dissolving LPS, IL-1β and IFN-γ in a medium for proliferating vascular endothelial cells in respective amounts of 50 μL/well, followed by incubating the cells at 37° C. for 24 hours in a 5% v/v $CO_2$ incubator and assaying TNF-α in the resulting supernatant with ELISA. As a control, except for adding a fresh preparation of the medium for proliferating vascular endothelial cells in an amount of 50 μL/well in place of the adenosine or adenosine N1-oxide solution, cells were cultured under the same conditions as in the above, and the supernatant in each well was collected and assayed for TNF-α with ELISA. The results are in Table 6 in parallel.

tration-dependent manner. Referring to their inhibitory strengths, since, compared to the cases of being free of

TABLE 6

| Experiment group | ANO Concentration (μM) | Adenosine concentration (μM) | LPS Concentration (μg/mL) | Verotoxin concentration (ng/mL) | TNF-α Concentration (pg/mL) | Amount of expressed tissue factor | Amount of expressed VCAM-1 |
|---|---|---|---|---|---|---|---|
| 1 | 0 | 0 | 0 | 0 | 0 | 0 | 2,751 |
| 2 | 0 | 0 | 10 | 0 | 52.7 | 26.3 | 4,144 |
| 3 | 0.2 | 0 | 10 | 0 | 51 | 27.6 | 4,123 |
| 4 | 0.5 | 0 | 10 | 0 | 41.1 | 13.5** | 4,052 |
| 5 | 1 | 0 | 10 | 0 | 25.1** | 12.9** | 3,920 |
| 6 | 2 | 0 | 10 | 0 | 12.3** | 9.4** | 3,967 |
| 7 | 5 | 0 | 10 | 0 | 1.8** | 0** | 3,603* |
| 8 | 10 | 0 | 10 | 0 | ND | 0** | 2,823** |
| 9 | 0 | 1 | 10 | 0 | 53 | 27.1 | 3,824 |
| 10 | 0 | 2 | 10 | 0 | 49.2 | 26.6 | 3,957 |
| 11 | 0 | 5 | 10 | 0 | 40.3 | 13.9** | 3,609** |
| 12 | 0 | 10 | 10 | 0 | 31.1** | 4.5** | 2,823** |
| 13 | 0 | 0 | 0 | 100 | 29.5 | NT | NT |
| 14 | 0.5 | 0 | 0 | 100 | 18.1** | NT | NT |
| 15 | 1 | 0 | 0 | 100 | 8.2** | NT | NT |
| 16 | 2 | 0 | 0 | 100 | 1.3** | NT | NT |

ANO: Adenosine N1-oxide.
NT: Not tested.
There exists a significant difference against the case wherein the additive amount of ANO or adenosine in an experiment group with the addition of macrophage stimulating factor is zero
(*P < 0.05,
**P < 0.01).

As evident from the results in Table 6, when HUVEC cells were cultured with the addition of LPS in the coexistence of IL-1β and IFN-γ, the production inhibition of TNF-α was observed depending on the concentration of adenosine and adenosine N1-oxide. Based on the result, comparing their $IC_{50}$ against their production inhibition of TNF-α, the $IC_{50}$ of adenosine N1-oxide is 0.97 μM, while that of adenosine is 15.2 μM, meaning that the TNF-α production inhibitory action of adenosine N1-oxide is stronger than that of adenosine by about 16 times.

Experiment 6-2

Influence on the Expression of Tissue Factor

To confluent HUVEC cells was added a solution of adenosine (a reagent-grade specimen commercialized by Wako Pure Chemical Industries Ltd., Tokyo, Japan) or adenosine N1-oxide, which had been dissolved in a medium for proliferating vascular endothelial cells to give the concentrations shown in Table 6, in an amount of 50 μL/well, followed by incubating the cells at 37° C. for 30 min in a 5% v/v $CO_2$ incubator. Thereafter, a solution of LPS, IL-1β, and IFN-γ were respectively prepared to give respective concentrations of 10 μg/mL, 2 ng/mL, and 500 IU/mL, added to the cells in an amount of 50 μL/well, and incubated at 37° C. for 5.5 hours in a 5% v/v $CO_2$ incubator. After the culture, the cells were washed twice with PBS, followed by adding PBS to the resulting cells in a volume of 50 μL/well. The multi-plates were subjected to a freezing at −80° C. and thawing process thrice, followed by adding 50 mM Tris buffer (pH 7.4) containing 100 mM NaCl and 0.2% Triton X-100 to the microplates in an amount of 50 μL/well, culturing the cells at 4° C. overnight to prepare a cell lysate. The content of tissue factor in the cell lysate was determined by "AssayMax Human Tissue Factor ELISA Kit", a product name of ELISA commercialized by Assay Pro, USA. The result is shown in Table 6 in parallel.

As evident from Table 6, the expression level of tissue factor induced in the presence of LPS, IL-1β, and INF-γ was inhibited by adenosine N1-oxide or adenosine in a concentration-dependent manner. Referring to their inhibitory strengths, since, compared to the cases of being free of adenosine N1-oxide or adenosine, the concentrations of adenosine N1-oxide and adenosine, which significantly inhibited the expression of tissue factor, were respectively at least 0.5 μM and at least 5 μM, adenosine N1-oxide is stronger than adenosine by at least 10 times. It is said that, when activated by microbial infection such as microorganisms, yeasts, and viruses, and by inflammatory cytokines including TNF-α, vascular endothelial cells express tissue factor or cell-adhesion factor on their cell surfaces and become susceptible to induce thrombosis. Therefore, the results show that adenosine N1-oxide inhibits thrombosis through the suppression of the production of tissue factor or cell-adhesion factor that relates to thrombosis, indicating that adenosine N1-oxide is useful as a therapeutic and prophylactic agent for infectious diseases wherein thrombosis such as disseminated intravascular coagulation (DIC) and systemic inflammatory response syndrome (SIRS) is considered as a main causative of exacerbation of symptoms.

Experiment 6-3

Influence on the Expression of Cell-Adhesion Factor

To the culture wells with confluent HUVEC cells were added both a solution of adenosine (a reagent-grade specimen commercialized by Wako Pure Chemical Industries Ltd., Tokyo, Japan) or adenosine N1-oxide, which had been dissolved in a medium for proliferating vascular endothelial cells to give the concentrations shown in Table 6, and a solution of LPS, IL-1β, and IFN-γ, which had been respectively prepared to give final concentrations of 10 μg/mL, 2 ng/mL, and 500 IU/mL, added to the cells in respective amounts of 50 μL/well, followed by incubating the cells at 37° C. for 5.5 hours in a 5% v/v $CO_2$ incubator. Thereafter, the supernatant in each well was removed by suction, and the cells were washed twice with PBS, followed by adding 4% paraformaldehyde to the cells and allowing them to stand at ambient temperature for one hour to fix them. After the fixation, the cells were washed thrice with PBS, followed by adding PBS containing 1% BSA and 0.05% $NaN_3$ in an amount of 150 μL/well, and subjecting the cells to blocking at 4° C. overnight. After the blocking, the solution in each well was removed, followed by adding "Human VCAM-1/CD106 Biotinylated Affinity-Purified Polyclonal Antibody Sheep IgG", a biotin-labeled sheep anti-human VCAM-1 polyclonal antibody commercialized by R & D Systems Inc., MN, USA, which had been prepared to give a concentration of 0.4 μg/mL with PBS containing 3% BSA, to the wells in an amount of 100 μL/well and allowing the cells to stand at ambient temperature for 1.5 hours. Thereafter, the cells were washed four times with PBS, adding an HRPO-labeled streptavidin ("Streptavidin HRP Conjugate", a product name of Invitrogen Corporation, CA, USA), which had been diluted with PBS containing 3% BSA by 1,000 times, in an amount of 100 μL/well and allowing the cells to stand at ambient temperature for one hour. Finally, the cells were washed four times with PBS, allowed to develop color for 10 min with "QuantaBlue™ Fluorogenic Peroxidase Substrate", commercialized by Pierce Biotechnology, IL, USA, and determined the cells' fluorescent intensity at a wavelength of 325 to 420 nm. As a control, cells were cultured and determined their fluorescent intensity under the same conditions as in the above, except for adding a medium for proliferating vascular endothelial cells in an amount of 50 μL/well to the cells in place of the solution of adenosine or adenosine N1-oxide. The results are in Table 6 in parallel.

As evident from Table 6, the expression level of cell-adhesion factor induced in the presence of LPS, IL-1β, and IFN-γ was inhibited by adenosine N1-oxide or adenosine in a concentration-dependent manner. Referring to their inhibitory strength, it can be speculated that there is no significant difference between them because an inhibitory tendency of the expression level is observed at a level of 5 μM or more in both cases.

Experiment 6-4

Influence of Verotoxin I on Cytopathy

Since adenosine N1-oxide was revealed to inhibit the production of inflammatory cytokines from macrophages by the stimulation of verotoxin in Experiment 3, the influence of adenosine N1-oxide on the production of inflammatory cytokines from vascular endothelial cells by the stimulation of verotoxin. The TNF-α production level by HUVEC cells was assayed with the same method as in Experiment 6-1 except for that verotoxin I, commercialized by Nacalai Tesque Inc., Kyoto, Japan, was added to give the same concentrations as shown in Table 6, in place of the stimulation of LPS/IL-1β/IFN-γ. The results are in Table 6 in parallel.

As evident from Table 6, adenosine N1-oxide effectively inhibited the TNF-α production level of HUVEC cells.

Piecing together the results in Experiment 6, it is suggested that one of the inhibitory mechanisms of bacterial shock induced by the addition of adenosine N1-oxide that was confirmed in Experiment 1 inhibits both the production of TNF-α, an inflammatory cytokine, from vascular endothelial cells and the expression of tissue factor and cell-adhesion factor in vascular endothelial cells. The inhibitory level is stronger than that of adenosine by 10 times and it is well coincided with the result in Experiment 2 using macrophages. Since it has been considered that verotoxin acts on vascular endothelial cells and produces inflammatory cytokines to disorder vascular endothelial cells and to induce hemorrhagic colitis and hemolytic-uremic syndrome, the above results show that adenosine N1-oxide inhibits the disorder of vascular endothelial cells by verotoxin and therefore it is useful as prophylactic and therapeutic agents for hemorrhagic colitis and hemolytic-uremic syndrome.

Experiment 7

<Influence of the Administration of Adenosine N1-Oxide on the Production of Cytokines Induced by the Administration of LPS>
<Test Method>

Since Experiment 1 confirmed that the administration of adenosine N1-oxide inhibits bacterial shock by the administration of LPS, and Experiments 2 to 6 suggested that such inhibitory mechanism is due to the action of inhibiting the production of TNF-α from macrophages and vascular endothelial cells by adenosine N1-oxide, it was conducted in this experiment a test for confirming that the administration of adenosine N1-oxide inhibits the production of inflammatory cytokines induced when LPS is actually administered to mice to induce bacterial shock. Since adenosine N1-oxide was suggested to possibly influence on the production on inflammatory cytokines other than TNF-α, it was further examined its effect on the production of IL-6 and IL-12 as inflammatory cytokines and of IL-10 as an anti-inflammatory cytokine. More specifically, 18 BALB/c female mice, 9-week-old, commercialized by Japan Charles River, Tokyo, Japan, were randomly divided into three groups, six heads each. An LPS specimen derived from *E. coli* (055:B5), commercialized by Sigma-Aldrich Corporation, St. Louis, Mo. USA, was dissolved in physiological saline and intraperitoneally administered to all the 6 mice in respective three groups at a dose of 18 mg/kg body weight of LPS (Experiment groups 1 to 3). Among the three groups, the six mice in one group were intravenously administered, simultaneously with the administration of LPS, with adenosine N1-oxide (ANO), which had been dissolved in PBS, in a liquid volume of 0.2 mL/head to give a dose of 68 mg/kg body weight of ANO (Experiment group 2). To the six mice of another one group was intravenously administered adenosine N1-oxide (ANO), which had been dissolved in PBS, in a liquid volume of 0.2 mL/head to give a dose of 135 mg/kg body weight of ANO (Experiment group 3), simultaneously with the administration of LPS. To the six mice of the remaining one group was intravenously administered PBS in a liquid volume of 0.2 mL/head simultaneously with the administration of LPS (Experiment group 1).

For the mice in each group, they were collected blood at two hours after the LPS administration, followed by assaying the level of TNF-α, IL-6, IL-10, and IL-12 in each serum and averaging the data for each group. The results are in Table 7. For the assay of the level of TNF-α, the same ELISA as in Experiment 2 was used and for the assay of the level of IL-6, the same ELISA as in Experiment 3 was used. For the assay of IL-10, it was used an ELISA for assaying it by an HRPO-labeled streptavidin, which uses "Rat Anti-Mouse IL-10 Antibody (Product code: 554421)", a product name of a commercialized rat-anti-mouse IL-10 antibody, commercialized by DB PharmiGene, Inc., Xizhi, Taiwan, as a solid phase antibody; and "Biotin-Labeled Rat Anti-Mouse IL-10 Antibody (Product code: 554423)", a product name of a commercialized biotin-labeled rat-anti-mouse IL-10 antibody commercialized by BD PharmiGene, Inc., Xizhi, Taiwan, as a secondary antibody. For the assay of IL-12, it was used an ELISA for assaying it by an HRPO-labeled streptavidin, which uses "Rat Anti-Mouse IL-12p70 Antibody (Product code: 554658)", a product name of a commercialized rat-anti-mouse IL-12 antibody, commercialized by DB PharmiGene, Inc., Xizhi, Taiwan, as a solid phase antibody; and "Biotin-Labeled Rat Anti-Mouse IL-12p70 Antibody (Product code: 51-26192E)", a product name of a commercialized biotin-labeled rat anti-mouse IL-10 antibody commercialized by BD PharmiGene, Inc., Xizhi, Taiwan, as a secondary antibody.

TABLE 7

| Experiment group | Dose of LPS (mg/kg body weight) | Dose of ANO (mg/kg body weight) | TNF-α Concentration (pg/mL) | IL-6 Concentration (ng/mL) | IL-10 Concentration (ng/mL) | IL-12 Concentration (pg/mL) |
| --- | --- | --- | --- | --- | --- | --- |
| 1 | 18 | 0 | 755 | 73.0 | ND | 268 |
| 2 | 18 | 68 | 109** | 59.1 | 14.1 | 136** |
| 3 | 18 | 135 | 46** | 46.3* | 19.3 | 105** |

ANO: Adenosine N1-oxide
ND: Below the detection limit
There exists a significant difference against experiment group 1
(*P < 0.05,
**P < 0.01).
Significance test for IL-10 was not done.

As evident from Table 7, TNF-α, IL-6, and IL-12 were detected in the mouse serum at two hours after the LPS administration but not IL-10 (Experiment group 1). On the contrary, compared to the case with no administration of adenosine N1-oxide, the TNF-α production in the serum of the mice administered, simultaneously with LPS, with 68 mg/kg body weight or 135 mg/kg body weight of adenosine N1-oxide was significantly inhibited by adenosine N1-oxide in a dose-dependent manner (Experiment groups 2 and 3). Similar to TNF-α, the formation of IL-6 and IL-12 were significantly inhibited by adenosine N1-oxide in a dose-dependent manner, but the formation of IL-10 as an anti-inflammatory cytokine was augmented by the administration of adenosine N1-oxide in a dose-dependent manner. TNF-α, IL-6, and IL-12 are said to be effector molecules that relate to the formation of clinical state of bacterial shock, and based on the results and those in Experiments 2 and 3, it can be concluded that a bacterial shock induced by the LPS administration was inhibited by the administration of adenosine N1-oxide, i.e., the reduction of survival rate of mice was inhibited by inhibiting the production of IL-6 and IL-12 as inflammatory cytokines, in addition to TNF-α as an inflammatory cytokine induced by LPS. Further, the fact that the augmentation of the production of IL-10 as an anti-inflammatory cytokine by the administration of adenosine N1-oxide can be speculated to contribute to the inhibition of reduction of survival rate of mice.

Experiment 8

<Influence 2 of the Administration of Adenosine N1-Oxide on Bacterial Shock>

In Experiment 1, the administration of adenosine N1-oxide was confirmed to inhibit bacterial shock in mice when administered simultaneously with LPS. Since bacterial shock promptly proceeds and it may possibly be treated with therapeutic agents in the advanced and exacerbated stage of clinical condition, the influence of the administration of adenosine N1-oxide on mice that had already suffered from bacterial shock and had exacerbated sepsis was examined in this experiment. That is to say, 14 BALB/c mice (9-week-old, female, commercialized by Charles River Laboratories Japan Inc., Tokyo, Japan) were randomly grouped into two groups, seven heads each (Experiment groups 1 and 2). An LPS specimen derived from *E. coli* (055:BB), commercialized by Sigma-Aldrich Corporation, St. Louis, Mo. USA, was dissolved in PBS and intraperitoneally administered to all the seven mice in each group at a dose of 18 mg/kg body weight of LPS. At one hour after administering LPS, seven mice in one group were intravenously administered with adenosine N1-oxide (ANO), which had been dissolved in PBS, at a dose of 135 mg/kg body weight in a liquid volume of 0.2 mL/head (Experiment group 2), while the remaining seven mice in the other group were intravenously administered with PBS in a volume of 0.2 mL/head (Experiment group 1). For each group, the survival number of mice was confirmed up to 7 to 27 hours after administering LPS and determined the survival rate (%) of mice in each group. The results are in Table 8.

TABLE 8

| Experiment group | Dose of LPS (mg/kg body weight) | Dose of ANO (mg/kg body weight) | Number of mice (head) | Survival rate (%) of mice | | |
| --- | --- | --- | --- | --- | --- | --- |
| | | | | 7 Hours | 22 Hours | 27 Hours |
| 1 | 18 | 0 | 7 | 100 | 14 | 14 |
| 2 | 18 | 135 | 7 | 100 | 86 | 57 |

ANO: Adenosine N1-oxide

As evident from Table 8, the survival rate of the mice administered with only LPS lowered to 14% at 22 hours after administering LPS (Experiment group 1). On the contrary, the mice administered with adenosine N1-oxide at one hour after administering PLS, the survival rate was 57% even at 27 hours after administering LPS (Experiment group 2), revealing that the death rate of mice induced by LPS was significantly lowered (P<0.05). The result in Experiment 7 indicates that adenosine N1-oxide can be used as a therapeutic agent in the case of having bacterial shock and exacerbated sepsis.

Experiment 9

<Influence of Adenosine or Inosine on Bacterial Shock>

It is known that adenosine N1-oxide is converted into inosine via adenosine in living bodies. Since adenosine N1-oxide was confirmed to be useful as a prophylactic or therapeutic agent for sepsis from the results in Experiments 1 to 8, a test for confirming whether adenosine or inosine as metabolites of adenosine N1-oxide have a similar effect or not. More specifically, 28 BALB/c mice (9-week-old, female, commercialized by Charles River Laboratories Japan Inc., Tokyo, Japan) were randomly grouped into four groups, seven heads each (Experiment groups 1 to 4). An LPS specimen derived from *E. coli* (055:B5), commercialized by Sigma-Aldrich Corporation, St. Louis, Mo. USA, was dissolved in PBS and intraperitoneally administered to all the seven mice in the four groups at a dose of 18 mg/kg body weight. Seven mice in one group were intravenously administered, simultaneously with LPS, with adenosine N1-oxide (ANO), which had been dissolved in PBS, at a dose of 135 mg/kg body weight in a liquid volume of 0.2 mL/head (Experiment group 2). Seven mice in each another two groups were intravenously administered, simultaneously with LPS, with adenosine (AN) or inosine (IN), which had been dissolved in PBS, at a dose of 127 mg/kg body weight in a liquid volume of 0.2 mL/head (Experiment groups 3 and 4). Seven mice in the remaining one group were intravenously administered with PBS as a control in a volume of 0.2 mL/head (Experiment group 1). For each group, the survival number of mice was confirmed up to 7 to 43 hours after administering LPS and the survival rate (%) of mice in each group was determined. The results are in Table 9.

TABLE 9

| Experiment group | Dose of LPS (mg/kg body weight) | Dose of ANO (mg/kg body weight) | Dose of AN (mg/kg body weight) | Dose of IN (mg/kg body weight) | Number of mice (head) | Survival rate (%) of mice | | | |
|---|---|---|---|---|---|---|---|---|---|
| | | | | | | 7 Hours | 19 Hours | 26 Hours | 43 Hours |
| 1 | 18 | 0 | 0 | 0 | 5 | 100 | 40 | 20 | 0 |
| 2 | 18 | 135 | 0 | 0 | 5 | 100 | 80 | 80 | 80 |
| 3 | 18 | 0 | 127 | 0 | 5 | 100 | 20 | 0 | 0 |
| 4 | 18 | 0 | 0 | 127 | 5 | 100 | 60 | 40 | 20 |

ANO: Adenosine N1-oxide
AN: Adenosine
IN: Inosine

As evident from Table 9, the survival rate of the mice (Experiment group 3) administered, simultaneously with LPS, with adenosine was similarly decreased with time as the mice (Experiment group 1) administered, simultaneously with LPS, with PBS. While, the survival rate of the mice (Experiment group 4) administered, simultaneously with LPS, with inosine hovered at a higher rate than the mice (Experiment group 1) administered, simultaneously with LPS, with PBS. On the contrary, the survival rate of the mice (Experiment 2) administered, simultaneously with LPS, with adenosine N1-oxide was confirmed to be significantly (P<0.05) improved compared to the mice in Experiments 1, 3 and 4. Based on the result, adenosine N1-oxide can be concluded to have a higher prophylactic or therapeutic effect on sepsis than adenosine and inosine.

Experiment 10

<Influence of the Oral Administration of Adenosine N1-Oxide on Bacterial Shock>

Since the intravenous administration of adenosine N1-oxide was revealed to effectively inhibit endotoxin shock in Experiment 1, a test to confirm that the oral administration of adenosine N1-oxide has also a similar effect to the case administered therewith intravenously. In particular, 32 BALB/c mice, (9-week-old, female, commercialized by Charles River Laboratories Japan Inc., Tokyo, Japan) were randomly grouped into four groups, eight heads each (Experiment groups 1 to 4). An LPS specimen derived from E. coli (055:B5), commercialized by Sigma-Aldrich Corporation, St. Louis, Mo. USA, which had been dissolved in PBS, was intraperitoneally administered to all the mice at a dose of 18 mg/kg body weight/head (Experiment groups 1 to 3). Among which, the eight mice in one group were orally administered through a gastric tube with adenosine N1-oxide, which had been dissolved in PBS, at a dose of 200 mg/kg body weight/shot in a liquid volume of 0.2 mL/head/shot at one hour before and after administering LPS (Experiment 2). Eight mice in another one group were administered through a gastric tube with adenosine N1-oxide, which had been dissolved in PBS, at a dose of 200 mg/kg body weight/shot in a liquid volume of 0.2 mL/head/shot at one hour before and after administering LPS and at 7 hours after the administration (Experiment group 2). The eight mice of the remaining one group were orally administered through a gastric tube with PBS in a liquid volume of 0.2 mL/head/shot (Experiment group 1). For each group, the survival number of mice was macroscopically observed up to 7 to 46 hours after administering LPS, and the survival rate (%) of mice in each group was determined. The results are in Table 10. The survival rate (%) of mice was similarly determined as in Experiment 1.

The influence of α-glucosyl-adenosine N1-oxide on bacterial shock was examined under the same conditions as in Experiment 3 except for using α-glucosyl-adenosine N1-oxide in place of adenosine N1-oxide used in Experiment 3 (Experiment group 4). The results are in Table 10 in parallel. For comparison, as α-glucosyl-adenosine N1-oxide, 3'-glucosyl-adenosine N1-oxide and 5'-glucosyl-adenosine N1-oxide with a purity of up to 98% or higher were used prepared by the steps of allowing a cyclomaltodextrin glucanotransferase derived from Geobacillus stearothermophilus Tc-91 strain (deposited under the accession number of FERM BP-11273 with AIST Tsukuba Central 6, 1-1, Higashi 1-chome, Tsukuba-shi, Ibaraki-ken, 305-8566 Japan, under the accession number of FERM BP-11273) to act on a solution containing adenosine and dextrin; allowing a glucoamylase specimen (a product name of "GLUCOZYME #20000", 20,000 units/g), commercialized by Nagase ChemteX Corp., Osaka, Japan; purifying the resulting reaction solution through a purification step including chromatographic separation to prepare 3'-glucosyl-adenosine and 5'-glucosyl-denosine with a purity of up to 98% or higher (see, for example, Japanese Patent Application No. 2011-20233); oxidizing the above compounds with hydrogen peroxide solution by the same method as in Experiment 1; and purifying the resulting compounds with column chromatography using "YMC-PACK R & D ODS-A COLUMN", a column for reverse-phase column chromatography, commercialized by YMC Co., Ltd., Kyoto, Japan.

TABLE 10

| Experiment group | Dose of LPS (mg/kg body weight) | Dose of ANO (mg/kg body weight) | Dose of 3'-G-ANO (mg/kg body weight) | Dose of 5'-G-ANO (mg/kg body weight) | Number of mice (head) | Survival rate (%) of mice | | | | | |
|---|---|---|---|---|---|---|---|---|---|---|---|
| | | | | | | 72 Hours | 22 Hours | 31 Hours | 46 Hours | 55 Hours | 79 Hours |
| 1 | 18 | 0 | 0 | 0 | 8 | 100 | 62.5 | 37.5 | 25 | 25 | 12.5 |
| 2 | 18 | 400 (200 × 2 shots) | 0 | 0 | 8 | 100 | 75 | 75 | 50 | 50 | 50 |

TABLE 10-continued

| Experiment group | Dose of LPS (mg/kg body weight) | Dose of ANO (mg/kg body weight) | Dose of 3'-G-ANO (mg/kg body weight) | Dose of 5'-G-ANO (mg/kg body weight) | Number of mice (head) | Survival rate (%) of mice | | | | |
|---|---|---|---|---|---|---|---|---|---|---|
| | | | | | | 72 Hours | 22 Hours | 31 Hours | 46 Hours | 55 Hours | 79 Hours |
| 3 | 18 | 600 (200 × 3 shots) | 0 | 0 | 8 | 100 | 87.5 | 87.5 | 87.5 | 87.5 | 75 |
| 4 | 18 | 0 | 400 (200 × 2 shots) | 0 | 8 | 100 | 50 | 50 | 37.5 | 37.5 | 37.5 |
| 5 | 18 | 0 | 600 (200 × 3 shots) | 0 | 8 | 100 | 75 | 62.5 | 62.5 | 50 | 50 |
| 6 | 18 | 0 | 0 | 400 (200 × 2 shots) | 8 | 100 | 62.5 | 37.5 | 25 | 12.5 | 12.5 |
| 7 | 18 | 0 | 0 | 600 (200 × 3 shots) | 8 | 100 | 62.5 | 50 | 37.5 | 37.5 | 25 |

ANO: Adenosine N1-oxide
3'-G-ANO: 3'-α-Glucosyl-asdenosine N1-oxide
5'-G-ANO: 5'-α-Glucosyl-asdenosine N1-oxide As evident from Table 10, the survival rate of the mice, administered with adenosine N1-oxide twice at a dose of 200 mg/kg body weight/shot, was 50% (Experiment group 2) at 79 hours after administering LPS. The survival rate of the mice, administered with adenosine N1-oxide thrice at a dose of 200 mg/kg body weight/shot, was 75% (Experiment group 3) at 79 hours after administering LPS. On the contrary, the survival rate of the mice, administered with only PBS, decreased to 12.5% (Experiment group 1) at 79 hours after administering LPS. The results indicate that the oral administration of adenosine N1-oxide attains an inhibitory effect on endotoxin shock similarly as in the case of intravenous administration. The survival rate of the mice, administered thrice with 3'-glucosyl-adenosine N1-oxide at a dose of 200 mg/kg body weight/shot, was 50% (Experiment group 5) at 79 hours after administering LPS. The group administered with 5'-glucosyl-adenosine N1-oxide (Experiment group 6) showed a substantially the same survival rate reduction as in a control (Experiment group 1). The result indicates that, when orally taken, α-glucosyl-adenosine N1-oxide forms adenosine N1-oxide through hydrolysis in the intestine to inhibit endotoxin shock similarly as in the case of taking adenosine N1-oxide, revealing that 3'-glucosyl-adenosine N1-oxide is useful as a therapeutic agent for sepsis similarly as in taking adenosine N1-oxide. Comparing the transition of survival rate with time and the dose, it can be considered that adenosine N1-oxide has a stronger action of inhibiting endotoxin shock than 3'-glucosyl-adenosine N1-oxide.

Experiment 11

<Influence of the Oral Administration of Adenosine N1-Oxide on the Production of Cytokine in Mouse Administered with LPS>

Since, in Experiment 10, the oral administration of adenosine N1-oxide inhibited the endotoxin shock induced by LPS administration, a test for confirming the fact that the oral administration of adenosine N1-oxide inhibits the production of inflammatory cytokines induced by LPS administration. In particular, 28 BALB/c mice (11-week-old, female, commercialized by Charles River Laboratories Japan Inc., Tokyo, Japan) were randomly divided into four groups, seven heads each (Experiment groups 1 to 4). The seven mice of one of these groups were administered through a gastric tube with adenosine N1-oxide, which had been dissolved in PBS, at a dose of 100 mg/kg body weight in a liquid volume of 0.2 mL/head (Experiment group 2). The seven mice of another one group were orally administered through a gastric tube with adenosine N1-oxide, which had been dissolved in PBS, at a dose of 200 mg/kg body weight in a liquid volume of 0.2 mL/head (Experiment group 3). The seven mice in another one group were orally administered through a gastric tube with 3'-glucosyl-adenosine N1-oxide, which had been dissolved in PBS, at a dose of 200 mg/kg body weight in a liquid volume of 0.2 mL/head (Experiment group 4). The seven mice in the remaining one group were orally administered through a gastric tube with PBS in a liquid volume of 0.2 mL/head (Experiment group 1). All the mice were intraperitoneally administered with an LPS specimen derived from *E. coli* (O55:B5), commercialized by Sigma-Aldrich Corporation, St. Louis, Mo. USA, which had been dissolved in PBS, at a dose of 18 mg/kg body weight (Experiment groups 1 to 4). For each group, the mice were collected blood from their tail veins at 90 min after administering LPS, followed by assaying the concentrations of TNF-α, IL-6, and IL-10 contained in serum by the same method as in Experiment 11. The results are in Table 11.

TABLE 11

| Experiment group | Dose of LPS (mg/kg body weight) | Dose of ANO (mg/kg body weight) | Dose of 3'-G-ANO (mg/kg body weight) | Amount of TNF-α (pg/mL) | Amount of IL-6 (ng/mL) | Amount of IL-10 (ng/mL) |
|---|---|---|---|---|---|---|
| 1 | 18 | 0 | 0 | 3060 | 19.4 | 2.7 |
| 2 | 18 | 100 | 0 | 1339 | 17.5 | 5.6* |
| 3 | 18 | 200 | 0 | 874* | 16.0* | 9.7** |
| 4 | 18 | 0 | 200 | 964* | 16.4* | 7.8* |

ANO: Adenosine N1-oxide
3'-G-ANO: 3'-Glucosyl-adenosine N1-oxide
There exists a significant difference against Experiment group 1
(*P < 0.05,
**P < 0.01).

As evident from Table 11, compared to the mice orally administered with PBS (Experiment group 1), the concentrations of TNF-α and IL-6 in the sera of the mice, which had been administered with adenosine N1-oxide or 3'-glucosyl-adenosine N1-oxide at a dose of 200 mg/kg body weight (Experiment groups 3 and 4), significantly decreased but the concentration of IL-10 significantly increased. Compared to the mice orally administered with PBS (Experiment group 1), the concentrations of TNF-α and IL-6 in the sera of the mice administered with adenosine N1-oxide at a dose of 100 mg/kg body weight (Experiment group 2) tended to decrease but the concentration of IL-10 significantly increased. The results indicate that one of the mechanisms of endotoxin shock inhibitory action by the oral administration of adenosine N1-oxide and 3'-glucosyl-adenosine N1-oxide is due to the action of inhibiting the production of TNF-α and IL-6 as inflammatory cytokines and of enhancing the production of IL-10 as an anti-inflammatory cytokine, similarly as in the case of the intravenous administration.

Experiment 12

<Influence of the Administration of Adenosine N1-Oxide on Hepatitis>

In this experiment, the influence of the administration of adenosine N1-oxide on liver disorder in which TNF-α is involved was examined by using mice with concanavalin A (Con A) induced liver disorder frequently used as a model animal for human autoimmune hepatitis and viral hepatitis (see, for example, "*Proceedings of the National Academy of Sciences of the United States of America*", Vol. 97, No. 10, pp. 5498-5503, 2000). In particular, 30 BALB/c mice (9-week-old, female, commercialized by Charles River Laboratories Japan Inc., Tokyo, Japan) were randomly divided into six groups, five heads each (Experiment groups 1 to 6). "TYPE IV", a Con A specimen commercialized by Sigma-Aldrich Corporation, St. Louis, Mo. USA, was dissolved in physiological saline and intravenously administered to all the five mice in each six groups at a dose of 15 mg/0.2 mL. The five mice in each three groups were intravenously administered, simultaneously with Con A, with adenosine N1-oxide, which had been dissolved in physiological saline, at a dose of 45 mg, 75 mg, or 135 mg/kg body weight (Experiment groups 2 to 4). The five mice in each another two groups were intravenously administered, simultaneously with Con A, with adenosine (AN) (Experiment group 5) or inosine (IN) (Experiment group 6), which had been dissolved in physiological saline, at a dose of 127 mg/kg body weight. The five mice in the remaining one group as a control were intravenously administered with 0.2 mL/head of physiological saline, simultaneously with Con A (Experiment group 1).

For the mice in each group, they were collected blood at 20 hours after administering Con A, followed by assaying the activity of GPT and GOT in their sera with "TRANSAMINASE CII-TEST WAKO", a commercialized assay kit produced by Wako Pure Chemical Industries Ltd., Tokyo, Japan, for use as an index for liver disorder due to hepatitis. The results are in Table 12. In parallel, the mice of the control (Experiment group 1), those administered with adenosine N1-oxide at a dose of 45 mg/kg body weight (Experiment group 2) or 135 mg/kg body weight (Experiment group 4), and those with adenosine or inosine at a dose of 127 mg/kg body weight (Experiment groups 5 and 6) were collected blood and anatomized to collect livers, followed by preparing tissue specimens in usual manner. The tissue specimens were stained with hematoxylin-eosin staining, followed by calculating an average of scores for judgement on the conditions of necrosis of liver tissues by microscopic observation, for use as an index for liver disorder. The results are in Table 12 in parallel. The conditions of necrosis of liver tissues were evaluated based on a microscopic observation standard of three grades of "mild (1)", "moderate (2)", and "severe (3)" and scored before determining the average for each group.

TABLE 12

| Experiment group | Dose of Con A (mg/kg body weight) | Dose of ANO (mg/kg body weight) | Dose of AN (mg/kg body weight) | Dose of IN (mg/kg body weight) | Number of mice (head) | Liver function GPT | Liver function GOT | Conditions of liver tissue Necrosis |
|---|---|---|---|---|---|---|---|---|
| 1 | 15 | 0 | 0 | 0 | 5 | 2836 | 8440 | 2.8 |
| 2 | 15 | 45 | 0 | 0 | 5 | 1477* | 2941++ | 2.4 |
| 3 | 15 | 75 | 0 | 0 | 5 | 1229* | 2654** | Not evaluated |
| 4 | 15 | 135 | 0 | 0 | 5 | 687** | 1343** | 2.0 |
| 5 | 15 | 0 | 127 | 0 | 5 | 1917 | 4130* | 2.5 |
| 6 | 15 | 0 | 0 | 127 | 5 | 2061 | 5243 | 2.6 |

ANO: Adenosine N1-oxide
AN: Adenosine
IN: Inosine
There exists a significant difference against Experiment group 1
(*$P < 0.05$,
**$P < 0.01$).

As evident from Table 12, compared to the control mice administered with only Con A (Experiment group 1), the liver disorder (elevated GOT and GPT levels) accompanied by hepatitis induced by the Con A administration was significantly inhibited depending on the dose of adenosine N1-oxide (Experiment groups 2 to 4). The necrosis of liver tissue was inhibited depending on the dose of adenosine N1-oxide. In the mice administered with adenosine (Experiment group 5) and with inosine (Experiment group 6), there was observed a tendency of improving the conditions of liver tissue and the disorder of liver function, though the level was weaker than those administered with adenosine N1-oxide, and those administered with adenosine exhibited a significant reduction of GOT compared to those with only Con A (Experiment group 1). The results indicate that adenosine N1-oxide is more useful as a prophylactic or therapeutic agent for liver disorder induced by hepatitis than adenosine and inosine.

Experiment 13

<Influence of the Administration of Adenosine N1-Oxide on Inflammatory Bowel Disease>

In this experiment, the influence of the administration of adenosine N1-oxide on inflammatory bowel disease in which TNF-α may be involved was examined by using mice with colitis induced by dextran sulfate sodium widely used as a model animal for human inflammatory bowel disease (see, for example, "*American Journal of Physiology*", Vol. 274, G544-G551, 1998). In particular, 45 C57BL/6 mice (9-week-old, female, commercialized by Charles River Laboratories Japan Inc., Tokyo, Japan) were randomly divided into five groups, eight heads each (Experiment groups 2 to 5) and another one group consisting of five mice (Experiment group 1). Dextran sulfate sodium (commercialized by MP Biomedicals, CA, USA, molecular weight of 36,000 to 50,000) was dissolved in tap water, and all the mice of these five groups consisting of eight heads each were allowed to freely take the solution for five days (Experiment groups 2 to 5). Among which, the eight mice of each of two groups were administered through a gastric tube with adenosine N1-oxide, which had been dissolved in PBS, at a dose of 33 or 100 mg/kg body weight once a day in a volume of 0.2 mL/head (Experiment groups 3 and 4) over 11 days ranging from the day (intake day 0) of initiating the intake of dextran sulfate sodium to $11^{th}$ day therefrom (intake day 10). The eight mice of each other two groups were administered through a gastric tube with adenosine (AN) or inosine (IN), which had been dissolved in PBS, at a dose of 94 mg/kg body weight once a day in an amount of 0.2 mL/head (Experiment groups 5 and 6) over 11 days ranging from the day (intake day 0) of initiating the administration of dextran sulfate sodium to $11^{th}$ day therefrom (intake day 10) (Experiment groups 5 and 6). The eight mice of the remaining one group were administered through a gastric tube with PBS once a day at a dose of 0.2 mL/head over 11 days from the day of initiating the administration of dextran sulfate sodium (Experiment group 2). The five mice of one group, which had not been administered with dextran sulfate sodium, were bred for 11 days on the normal feed while allowing them to take tap water freely (Experiment group 1).

The mice were weighed and their degree of diarrhea and hematochezia were macroscopically observed every day over 11 days from the day of initiating the intake of dextran sulfate sodium. The body weight reduction percentage (%) was determined by dividing the body weight of a mouse at $11^{th}$ day after initiating the intake of dextran sulfate sodium by the body weight of the mouse at the day of initiating the intake, and multiplying the value by 100, and subtracting the resulting value from 100. The scores of diarrhea and hematochezia and the body weight reduction percentage (%) in each mouse were scored according to the criteria as shown in Table 13. For each group, the average of the total scores of diarrhea and hematochezia on days ranging from the day (intake day 0) of initiating the intake of dextran sulfate sodium to $11^{th}$ day therefrom (intake day 10) are determined and shown in Table 14. The total scores of diarrhea, hematochezia, and body weight reduction percentage for each mouse at $11^{th}$ day (intake day 10) after initiating the intake of dextran sulfate sodium are calculated for disease activity index (DAI) used as an index for colitis, averaged for each group, and shown in Table 14. On $11^{th}$ day after initiating the intake of dextran sulfate sodium, each mouse was collected blood, followed by assaying haptoglobin or an acute phase protein, as an index for inflammatory, on an ELISA kit commercialized by Life Diagnostics USA, and averaging the data for each group. The results are in Table 14 in parallel. Since one mouse in Experiment group 2 administered with only dextran sulfate sodium was dead at $11^{th}$ day after initiating the intake of dextran sulfate sodium, the results of Experiment group 2 at $11^{th}$ day (intake day 10) after initiating the intake of dextran sulfate sodium represent the average of seven mice.

TABLE 13

| Score | Severity of diarrhea | Severity of hematochezia | Body weight reduction percentage (%) |
|---|---|---|---|
| 0 | Normal | Normal | ≤1 |
| 1 | Soft stool (Watery and shaped stool) | Stool tinged with blood | 1< ≤10 |
| 2 | Diarrhea stool (Watery and deformed stool) | Blood is attached to anus | 10< ≤20 |
| 3 | Watery diarrhea (Almost unshaped liquid stool) | Bleeding from anus all of the time | 20< ≤30 |
| 4 | | | 30< |

TABLE 14

| Experiment group | Intake of dextran sulfate sodium | Dose of ANO (mg/kg body weight) | Dose of AN (mg/kg body weight) | Dose of IN (mg/kg body weight) | Number of mice | Number of day(s) after initiating the intake of dextran sulfate sodium | | | | | | | | | | | | Content of haptoglobin (mg/mL) |
|---|---|---|---|---|---|---|---|---|---|---|---|---|---|---|---|---|---|---|
| | | | | | | 0 | 1 | 2 | 3 | 4 | 5 | 6 | 7 | 8 | 9 | 10 | 10 DAI# | |
| | | | | | | Total scores of diarrhea and hematochezia | | | | | | | | | | | | |
| 1 | No | 0 | 0 | 0 | 5 | 0 | 0 | 0 | 0 | 0 | 0 | 0 | 0 | 0 | 0 | 0 | 0 | 0.1> |
| 2 | Yes | 0 | 0 | 0 | 8 | 0 | 0 | 0 | 0.3 | 1.0 | 1.8 | 1.3 | 1.8 | 1.5 | 1.5 | 1.6 | 4.7 | 4.1 |
| 3 | Yes | 33 | 0 | 0 | 8 | 0 | 0 | 0 | 0 | 0.3 | 0.3 | 0.5 | 0.6 | 0.9 | 0.8 | 0.7 | 3.8* | 3.7 |
| 4 | Yes | 100 | 0 | 0 | 8 | 0 | 0 | 0 | 0.3 | 0.4 | 0.4 | 0.5 | 0.6 | 0.6 | 0.7 | 0.6 | 3.4** | 2.9* |
| 5 | Yes | 0 | 94 | 0 | 8 | 0 | 0 | 0 | 0.3 | 1.0 | 1.4 | 1.3 | 1.4 | 1.4 | 1.4 | 1.6 | 4.6 | 4.0 |
| 6 | Yes | 0 | 0 | 94 | 8 | 0 | 0 | 0 | 0.1 | 0.8 | 1.1 | 1.2 | 1.1 | 1.2 | 1.2 | 1.3 | 4.1 | 3.9 |

ANO: Adenosine N1-oxide
AN: Adenosine
IN: Inosine
DAI (total scores of diarrhea, hematochezia, and body weight reduction percentage)
There exists a significant difference against Experiment 2
(*P < 0.05,
**P < 0.01).

As evident from Table 14, the total scores of diarrhea stool and hematochezia of colitis induced by the intake of dextran sulfate sodium decreased depending on the dose of adenosine N1-oxide compared to the mice with only dextran sulfate sodium (Experiment group 2), observing that a significant (P<0.05) reduction at after 6$^{th}$ day (intake day 5) after initiating the intake of dextran sulfate sodium (Experiment groups 3 and 4). In these Experiment groups, the level of DAI, which is the total scores of diarrhea, hematochezia, and body weight reduction percentage from the day of initiating the intake of dextran sulfate sodium to 11$^{th}$ day after the initiation, and the level of haptoglobin showed a significant reduction (P<0.05) compared to the mice administered with only dextran sulfate sodium (Experiment group 2). In the group administered with adenosine (Experiment group 5), there was found no difference in the total scores of diarrhea and hematochezia and the levels of DAI and haptoglobin, compared to the mice with only dextran sulfate sodium (Experiment group 2). In the group administered with inosine (Experiment group 6), there was found a downward tendency but no significant difference was found in the total scores of diarrhea and hematochezia and in the levels of DAI and haptoglobin, compared to the mice with only dextran sulfate sodium (Experiment group 2). The results indicate that adenosine N1-oxide is more useful as a prophylactic or therapeutic agent for inflammatory diseases than adenosine and inosine.

Experiment 14

<Influence of the Administration of Adenosine N1-Oxide on Kidney Inflammation>

It is known that kidney inflammation is induced by various causatives and the deterioration of renal glomerulus is progressed as the disease progresses. In this experiment, the influence of the administration of adenosine N1-oxide on kidney inflammation was examined by using KK-Ay mice, which naturally develop type II diabetes and are widely used as a model animal for type II diabetes (see, for example, "Experimental Animals", Vol. 51, No. 2, pp. 191-196, 2002).

<Test Method>

Fifty KK-Ay mice, 5-week-old, male, commercialized by Japan Crea Co., Tokyo, Japan, were preliminary bred for one week on CE-2 feed commercialized by Japan Crea Co., Tokyo, Japan, measured for body weight and blood glucose level in blood samples collected from their tail veins, and randomly grouped into five groups, ten heads each, after balancing each measured value. One of the five groups was made into a control group and the mice of the group were allowed to take water freely and bred for 10 weeks (Experiment group 1). Two groups of the remaining four groups were allowed to freely take adenosine N1-oxide, which had been dissolved in drinking water, every day at a dose of 30 mg/kg body weight/day or 100 mg/kg body weight/day and bred for 10 weeks (Experiment groups 2 and 3). The mice of the remaining two groups were allowed to freely take either adenosine or inosine every day at a dose of 94 mg/kg body weight/day and bred for 10 weeks (Experiment groups 4 and 5). Throughout the periods of preliminary breeding and testing, the mice were bred while freely allowing them to take CE-2 feed at 22±2° C. under a light-dark cycle of 12 hours (lighting: from 7:00 to 19:00). At the termination of the test, the mice were evaluated based on their body weight, weight ratio of kidney, blood glucose level, hemoglobin A1c (HbA1c), and pathological findings of renal disorder by autopsy, and the percentage of mice with at least 50% consolidation (++) of renal glomerulus against the total glomus is shown in Table 15. The weight ratio of kidney was determined by dividing the weight of kidney by the body weight. The blood glucose level, HbA1c, and denatured score of renal glomerulus were determined by the following method.

<Methods for Measuring Laboratory Test Values and for Scoring Pathological Findings>

<Blood Glucose Level>

At the termination of the test, the mice were fasted for 16 hours prior to autopsy and collected blood from their postcava for measurement of fasting glucose level. The blood glucose level was determined by "GLUCOSE CII-TEST WAKO", a product name of a commercialized reagent for blood glucose level commercialized by Wako Pure Chemical Industries Ltd., Tokyo, Japan.

<HbA1c Level>

At the termination of the test, the mice were fasted for 16 hours before autopsy and collected blood from their postcava for measurement of interdigestive HbA1c level. The measurement was asked FALCO biosystems Ltd., Kyoto, Japan, a privately-owned clinical inspection institute.

<Evaluation of Pathological Tissue>

At the autopsy, each mouse was collected his kidney which was then fixed with neutral buffered formalin, prepared into a pathologic tissue section in usual manner, and stained with hematoxylin-eosin staining (H-E staining) and PAS staining. For the stained pathologic tissue section of each mouse, they were compared with that of the control and the pathological findings by microscopic observation were judged based on the following criteria and scored for an index of the denaturation of renal disorder.

<Method of Scoring Pathological Findings of Kidney>

The degree of renal disorder was judged based on the degree of consolidation of renal glomerulus: The degree was judged based on the four grades; (++), meaning that at least 50% consolidation of renal glomerulus is observed against the total glomus; (+), meaning that at least 25% but below 50% consolidation of renal glomerulus is observed against the total glomus; (±), meaning that less than 25% consolidation of renal glomerulus is observed against the total glomus; and (−), meaning that no consolidation of renal glomerulus is observed against the total glomus. The pathological findings of kidney was judged based on an evaluation criterion for pathologic tissue (see, for example, the lines 12 to 21 at page 862 of "American Journal of Pathology", Vol. 160, No. 3, pp. 861-867, 2002, by Andrea Hartner et al.).

TABLE 15

| Experiment group | Dose of ANO (mg/kg body weight) | Dose of AN (mg/kg body weight) | Dose of IN (mg/kg body weight) | Number of mice (head) | Body weight (g) | Weight ratio of kidney | Blood glucose level (mg/dL) | HbA1c value (%) | Percentage of subject with renal glomerulus solidification (++) (%) |
|---|---|---|---|---|---|---|---|---|---|
| 1 | 0 | 0 | 0 | 10 | 42.1 | 0.013 | 348 | 6.75 | 100 |
| 2 | 0 | 30 | 0 | 10 | 43.8 | 0.013 | 304 | 6.79 | 50 |

TABLE 15-continued

| Experiment group | Dose of ANO (mg/kg body weight) | Dose of AN (mg/kg body weight) | Dose of IN (mg/kg body weight) | Number of mice (head) | Body weight (g) | Weight ratio of kidney | Blood glucose level (mg/dL) | HbA1c value (%) | Percentage of subject with renal glomerulus solidification (++) (%) |
|---|---|---|---|---|---|---|---|---|---|
| 3 | 0 0 100 | 0 | 0 | 10 | 42.8 | 0.013 | 305 | 5.40* | 30 |
| 4 | 0 0 0 | 94 | 0 | 10 | 43.5 | 0.013 | 342 | 6.72 | 100 |
| 5 | 0 0 0 | 0 | 94 | 10 | 43.2 | 0.013 | 340 | 6.55 | 80 |

ANO: Adenosine N1-oxide
AN: Adenosine
IN: Inosine
There exists a significant difference against Experiment group 1
(*P < 0.05).
Weight ratio of kidney = (Weight of kidney)/(Body weight)

As evident from Table 15, the ratio of mice with a renal glomerulus solidification of 50% or more was significantly decreased to 50% for the mice administered with adenosine N1-oxide every day at a dose of 30 mg/kg body weight (Experiment group 2), and to 30% for the mice with a dose of 100 mg/kg body weight (Experiment group 3), compared to 100% for the group administered with only CE-2 feed (Experiment group 1). The group administered with adenosine every day at a dose of 94 mg/kg body weight (Experiment group 4) showed 100% as a ratio of mice with a renal glomerulus solidification of 50% or more and had no significant difference from the group administered with only CE-2 feed (Experiment group 1). The group administered with inosine every day at a dose of 94 mg/kg body weight (Experiment group 5) decreased to 80% as a ratio of mice with a renal glomerulus solidification of 50% or more. Among/between any Experiment groups, there was found no difference in body weight, weight ratio of kidney, and blood glucose level. The results indicate that adenosine N1-oxide is useful as a therapeutic agent for kidney inflammation that inhibits the consolidation (denaturation) of renal glomerulus induced by kidney inflammation. It is indicated that adenosine N1-oxide is also useful as a therapeutic agent for diabetes because the group administered with adenosine N1-oxide every day at a dose of 100 mg/kg body weight (Experiment group 3) exhibited an HbA1c value of 5.40% that was a significantly decreased level compared to 6.75% of the group with only CE-2 feed (Experiment group 1), and the groups administered with adenosine N1-oxide (Experiment groups 2 and 3) also tended to show a decreased blood glucose level compared to other Experiment groups.

Experiment 15

<Influence of the Administration of Adenosine N1-Oxide on Pancreatitis>

In this experiment, the influence of the administration of adenosine N1-oxide on pancreatitis disorder in which TNF-α is involved was examined by using a mouse with severe acute pancreatitis induced by choline-deficient ethionine-added feed that is widely used as a model animal for human pancreatitis (see, for example, "Journal of Pharmacology and Experimental Therapeutics", Vol. 328, No. 1, pp. 256-262, 2009). Forty CD1(ICR) mice, 3-week-old, female, commercialized by Charles River Laboratories Japan Inc., Tokyo, Japan, were randomly divided into five groups, eight heads each. After seven days of a preliminary breeding, the mice were fasted for one day and allowed to freely take a choline-deficient ethionine-added feed, produced by Oriental Yeast Co., Ltd., Tokyo, Japan, for three days from the next day. Thereafter, the mice were fed on normal feed again and then fed on the choline-deficient ethionine-added feed. Eight mice in one group were orally administered through a gastric tube with adenosine N1-oxide, which had been dissolved in distilled water, at a dose of 46 mg/kg body weight/shot in a liquid volume of 0.2 mL/head/shot twice a day every morning and evening from the initiation of fasting. Eight mice of another one group were orally administered through a gastric tube with adenosine N1-oxide, which had been dissolved in distilled water, twice a day every morning and evening at a dose of 139 mg/kg body weight/shot in a liquid volume of 0.2 mL/head/shot from the initiation of fasting. Eight mice in another two groups were orally administered through a gastric tube with adenosine or inosine, which had been dissolved in distilled water, twice a day every morning and evening at a dose of 124 mg/kg body weight/shot in a liquid volume of 0.2 mL/head/shot from the initiation of fasting. Eight mice in the remaining one group as a control were orally administered through a gastric tube with distilled water twice a day every morning and evening in a liquid volume of 0.2 mL/head/shot from the initiation of fasting. The survival number of mice in each group was macroscopically confirmed up to seven days from the initiation of taking the choline-deficient ethionine-added feed, and the survival rate (%) of mice in each group was determined. The results are in Table 16. The survival rate (%) of mice was determined similarly as in Experiment 1.

TABLE 16

| Experiment group | Dose of ANO (mg/kg body weight) | Dose of AN (mg/kg body weight) | Dose of IN (mg/kg body weight) | Number of mice (head) | Survival rate (%) of mice | | | | | |
|---|---|---|---|---|---|---|---|---|---|---|
| | | | | | 48 Hours | 70 Hours | 78 Hours | 94 Hours | 102 Hours | 144 Hours |
| 1 | 0 | 0 | 0 | 8 | 100.0 | 100.0 | 62.5 | 25.0 | 12.5 | 12.5 |
| 2 | 46 | 0 | 0 | 8 | 100.0 | 100.0 | 50.0 | 25.0 | 12.5 | 12.5 |
| 3 | 0 | 139 | 0 | 8 | 100.0 | 87.5 | 75.0 | 75.0 | 75.0 | 75.0 |

TABLE 16-continued

| Experiment group | Dose of ANO (mg/kg body weight) | Dose of AN (mg/kg body weight) | Dose of IN (mg/kg body weight) | Number of mice (head) | Survival rate (%) of mice | | | | | |
|---|---|---|---|---|---|---|---|---|---|---|
| | | | | | 48 Hours | 70 Hours | 78 Hours | 94 Hours | 102 Hours | 144 Hours |
| 4 | 0 | 0 | 124 | 0 | 8 | 100.0 | 20.0 | 50.0 | 25.0 | 12.5 | 12.5 |
| 5 | 0 | 0 | 0 | 124 | 8 | 100.0 | 60.0 | 62.5 | 50.0 | 25.0 | 12.5 |

ANO: Adenosine N1-oxide
AN: Adenosine
IN: Inosine

As evident from Table 16, when mice were orally administered through a gastric tube with adenosine N1-oxide, which had been dissolved in distilled water, twice a day every morning and evening at a dose of 139 mg/kg body weight/shot in a liquid volume of 0.2 mL/head/shot, the reduction of survival rate of mice with acute pancreatitis induced by the intake of choline-deficient ethionine-added feed was significantly inhibited, compared to the control mice administered with only distilled water (Experiment group 1), and no death was observed at after 78 hours through 144 hours. The survival rate of the mice administered through a gastric tube with adenosine N1-oxide at a dose of 46 mg/kg body weight/shot or adenosine at a dose of 124 mg/kg body weigh/shot in a liquid volume of 0.2 mL/head/shot were decreased with time similarly as in the mice administered with only distilled water (Experiment group 1). The survival rate of the mice orally administered through a gastric tube with inosine at a dose of 124 mg/kg body weigh/shot in a liquid volume of 0.2 mL/head/shot tended to be more decreased than the mice administered with only distilled water (Experiment group 1), but decreased to the same survival rate as in the mice with only distilled water at 144 hours after initiating the intake of the choline-deficient ethionine-added feed. The result indicates that adenosine N1-oxide is useful as a prophylactic or therapeutic agent for pancreatitis and the therapeutic effect is superior to inosine.

Experiment 16

<Influence of Adenosine N1-Oxide on Atopic Dermatitis

In this experiment, the influence of the administration of adenosine N1-oxide on atopic dermatitis was examined by using picryl chloride-sensitized mice widely used as a model animal for human atopic dermatitis. The induction of the symptom of dermal inflammation was conducted according to a protocol of Charles River Laboratories Japan Inc., Tokyo, Japan. For reference, picryl chloride was purchased from Tokyo Chemical Industry Co., Ltd., Tokyo, Japan, and according to a protocol by Charles River Laboratories Japan Inc., Tokyo, Japan, it was dissolved in ethanol and recrystallized for use.

<Test Method>

Forty-eight NC/Nga mice, 6-week-old, female, commercialized by Charles River Laboratories Japan Inc., Tokyo, Japan, were shaved off their abdominal skins with an electric shaver and randomly divided into six groups, eight heads each. The eight mice in each five groups were sensitized (may be simply called "sensitization", hereinafter) with picryl chloride (Tokyo Chemical Industry Co., Ltd., Tokyo, Japan) in such a manner of dropping a solution, which had been dissolved in a mixture solution of ethanol and acetone in a volume ratio of 4:1 at a concentration of 5%, on the shaved abdominal skin of the mice and on four footpads in a total volume of 150 μL/mouse, and spreading the solution over the abdominal skin and the foot pads by using a micropipette similarly as above. On four days after the sensitization, the dorsal skin of the mice, which had been shaved off with an electric shaver on the previous day of the following application, were applied to induce dermatitis with 150 μL/mouse of picryl chloride, which had been dissolved in olive oil, commercialized by Wako Pure Chemical Industries Ltd., Tokyo, Japan, to give a concentration of one percent, by using a micropipette tip in such a manner similarly as in the above, and repeating a similar procedure as in the above five times at intervals of one week to induce dermatitis (may be simply called "induction", hereinafter) six times in total. The eight mice in one group were applied their dermatitis-induced dorsal skin parts on the days ranging from three days before the sensitization through until four days after the $6^{th}$ induction with 100 μL/mouse of a gel (14 mg/mL of adenosine N1-oxide), which had been prepared by mixing 2.2% adenosine N1-oxide and "HIVISWAKO", a product name of an aqueous carboxyvinyl polymer, commercialized by Wako Pure Chemical Industries Ltd., Tokyo, Japan, by using a micropipette tip similarly as in the above at a dose of 100 μL/mouse twice a day every morning and evening at a cycle of an application of successive five days and a resting of successive two days (Experiment group 2). The application of the gel containing adenosine N1-oxide was started on a Monday morning. The eight mice of two groups were applied their dorsal skin parts, where dermatitis had been induced by the same application schedule as in adenosine N1-oxide, with a gel containing 13 mg/mL gel of adenosine or inosine, which had been prepared by mixing a 2.1% adenosine or inosine solution and the above aqueous carboxyvinyl polymer (Experiment groups 3 and 4). The eight mice of the remaining one group, which had been sensitized with picryl chloride, as a positive control were applied their dorsal skin parts, which had been induced dermatitis by the same application schedule as in adenosine N1-oxide, with a gel containing 6.7 mg/mL gel of prednisolone, which had been prepared by mixing prednisolone 21-disodium phosphate, commercialized by Tokyo Chemical Industry Co., Ltd., Tokyo, Japan (called simply "prednisolone", hereinafter), with the above-identified aqueous carboxyvinyl polymer, twice a day every morning and evening at a cycle of an application of successive five days and a resting of successive two days to induce dermatitis from the Monday morning of the $3^{rd}$ induction week ($17^{th}$ day after initiating the application) through until four days after the $6^{th}$ induction (Experiment group 5). The remaining one group applied with picryl chloride as a control were applied with a gel, which had been prepared by adding refined water to the above-identified carboxyvinyl polymer, at the same schedule as in adenosine N1-oxide (Experiment group 1). The eight mice in the remaining one group as a normal group were bred without applying picryl chloride or a gel to their abdominal or dorsal parts, which had been shaved off with an electric shaver, at the initiation of the test (Experiment group 6).

On Friday of the 6th week of the induction (46th day after initiating the application), all the mice were sacrificed, followed by isolating their spleens and collecting spleen cells in usual manner. The spleen cells were suspended in RPMI 1640 medium supplemented with 10% FCS and inoculated to 24-well plates to give a cell concentration of $5 \times 10^6$ cells/0.5 mL/well. To each well 2 µg/mL of "Purified Mouse CD3ε Monoclonal Antibody", a product name of an anti-CD3 antibody, commercialized by Cosmo Bio Co., Ltd., Tokyo, Japan, was added, and the cells were incubated at 37° C. for three days in a 5% v/v $CO_2$ incubator, followed by assaying the levels of cytokines in each supernatant thereof.

<Evaluation Method>

Throughout the test period, the mice were weighed once a week. The judgement of the conditions of skin inflammation was conducted twice a week every Tuesday and Friday from the 3rd induction for the degrees of four items of red flare/bleeding, edema (swelling of earflap), chafing/loss of tissue, and the formation of scar tissue/drying, and scored based on the criterion of four grades shown in Table 17; "0" (symptomless), "1" (mild), "2" (moderate), and "3" (severe). The total scores of each evaluation items for each group were averaged for use as a skin score. The skin score for Experiment groups 1 to 5, which had been sensitized with picryl chloride, are shown in Table 18. The concentrations of IL-4, IL-5, IL-6, and IFN-γ in the supernatant of each mouse's spleen cells stimulated with the anti-CD3 antibody were assayed with ELISA specific to each cytokine, followed by averaging the production levels for respective cytokines in spleen cells of the mice in each group. The results are in Table 19 in parallel.

TABLE 17

| Evaluation item | Score and its criterion for judgement | | | |
|---|---|---|---|---|
| | 0 (Symptomless) | 1 (Mild) | 2 (Moderate) | 3 (Severe) |
| Rate of erythema against the induced part | With no red flare | 1/2< | ≥2/3 | With red flare |
| Degree of bleeding | With no bleeding | With no bleeding | With no bleeding | With no bleeding |
| Degree of swelling of earflap when compared to normal mouse | None | Normally appeared, pressure-induced concave | Macroscopically observable edema | Intense edema and bleeding |
| Rate of the part of chafing/loss of tissue against the induced part | 0 | 1/3≤ | 1/3< ≥2/3 | <2/3 |
| Rate of the scabbing part against the induced part | 0 | 1/3≤ | 1/3< ≥2/3 | <2/3 |

TABLE 18

| Experiment group | Reagent added to applied gel | Number of mice (head) | Skin score (number of days after the day of sensitizing with picryl chloride) | | | | | | | |
|---|---|---|---|---|---|---|---|---|---|---|
| | | | 21 | 24 | 28 | 31 | 35 | 39 | 42 | 45 |
| 1 | Not added | 8 | 0.50 | 0.50 | 2.00 | 2.75 | 5.25 | 5.50 | 6.13 | 6.23 |
| 2 | ANO | 8 | 0.75 | 1.00 | 2.25 | 3.38 | 4.50 | 3.58* | 4.38* | 3.63* |
| 3 | AN | 8 | 0.50 | 0.50 | 2.75 | 3.55 | 5.56 | 5.78 | 6.22 | 5.50 |
| 4 | IN | 8 | 0.50 | 0.50 | 2.50 | 3.22 | 5.20 | 5.66 | 6.00 | 5.43 |
| 5 | Prednisolone | 8 | 0.38 | 0.63 | 0.75* | 1.25 | 1.38** | 2.63** | 2.75** | 3.13** |

ANO: Adenosine N1-oxide
AN: Adenosine
IN: Inosine
There exists a significant difference against Experiment group 1
(*P < 0.05,
**P < 0.01).

TABLE 19

| Experiment group | Sensitization by picryl chloride | Substance contained in applied gel | Content of IL-4 (ng/mL) | Content of IL-5 (ng/mL) | Content of IL-6 (ng/mL) | Content of IFN-γ (pg/mL) | Ratio of IL-4/IFN-γ |
|---|---|---|---|---|---|---|---|
| 1 | Yes | None | 10.3 | 217 | 202 | 11.5 | 0.90 |
| 2 | Yes | ANO | 2.8* | 157 | 129* | 8.75* | 0.32 |
| 3 | Yes | AN | 9.8 | 225 | 192 | 12.1 | 0.81 |
| 4 | Yes | IN | 9.3 | 209 | 150 | 13.2 | 0.70 |
| 5 | Yes | Prednisolone | NT | NT | NT | NT | — |
| 6 | No | None | 2.7 | 86 | 159 | 14.5 | 0.18 |

ANO: Adenosine N1-oxide
AN: Adenosine
IN: Inosine
NT: Not tested
There exists a significant difference against Experiment group 1
(*P < 0.05).

As evident from Table 18, the skin score of the mice applied with the gel containing adenosine N1-oxide (Experiment group 2) increased with time from 21 days after the sensitization with picryl chloride and tended to progress in skin inflammation, and the skin inflammation was significantly inhibited from 39 days after the sensitization, compared to the skin score of the mice applied with the gel prepared by adding refined water (Experiment group 1). In a part of the inflammation-induced skin, the regeneration of hair was observed and the cure/improvement of wounds induced by inflammation was observed. The skin score of the mice applied with the gel containing adenosine or inosine (Experiment groups 3 and 4) was substantially the same as in the mice applied with the gel prepared by adding refined water (Experiment group 1) and no improvement was observed by the application of these substances. The skin score of the mice (Experiment group 5), applied with the gel containing prednisolone known as an anti-inflammatory agent, was significantly lowered from 28 days after the sensitization compared to the mice (Experiment group 1) applied with the gel prepared by adding refined water, however, no recovery of skin wounds in the inflammation-induced part that had been observed in the application of adenosine N1-oxide was observed. For comparison, the body weight of mice applied with the gel containing adenosine N1-oxide showed a similar increment of body weight to the control mice applied with the gel prepared by adding refined water (Experiment group 1) throughout the test period of time, but no influence accompanied by the induction of inflammation was observed. On the contrary, the mice applied with the gel containing adenosine or inosine (Experiment groups 3 and 4) showed a reduction of increasing rate of their body weights that was deemed inherent to the stress by itching sensation in the inflammation-induced part, compared to the normal group treated with only shaving (Experiment group 6) after the week of the $2^{nd}$ induction (12 days after initiating the application). The mice applied with prednisolone as a positive control group (Experiment group 5) showed a significant reduction of body weight, deemed as a side effect of prednisolone, from the week at the $5^{th}$ induction, compared to the normal group mice (Experiment group 6) treated with only shaving of the abdominal and dorsal skin parts. The results indicate that adenosine N1-oxide is useful as a prophylactic and therapeutic agent for skin inflammation or as a prophylactic or therapeutic agent for wounds accompanied by the induction of inflammation. As evident from Table 19, when the spleen cells of the mice applied with the gel prepared by adding adenosine N1-oxide (Experiment group 2) were stimulated with the anti-CD3 antibody, the production level of any of IL-4, IL-5, IL-6, and IFN-γ was significantly lower than those of IL-4, IL-6, and IFN-γ when the spleen cells of the mice applied with the gel prepared by adding refined water (Experiment group 1) were stimulated with the anti-CD3 antibody and the production level of IL-5 also tended to decrease. When the spleen cells of the mice applied with the gel containing adenosine or inosine (Experiment groups 3 and 4) were stimulated with the anti-CD3 antibody, the production level of any of IL-4, IL-5, IL-6, and IFN-γ showed no difference from those in the case of that the spleen cells of the mice applied with the gel prepared by adding refined water (Experiment group 1) were stimulated with the anti-CD3 antibody. Comparing the production ratio of IL-4/IFN-γ of spleen cells, which had been prepared from the normal mice treated with only shaving (Experiment group 6) and from the mice applied with the gel prepared by adding refined water after being sensitized with picryl chloride (Experiment group 1), stimulated with the anti-CD3 antibody, it was confirmed that the latter mice showed a higher ratio and they became a Th2 predominant state that is characteristic to atopic diseases. It shows that, since the production ratio of IL-4/IFN-γ, which were produced when the spleen cells of the mice that had been applied with adenosine N1-oxide (Experiment group 2) and stimulated with the anti-CD3 antibody, was close to that of the mice of the normal group treated with only shaving (Experiment group 6), the application of adenosine N1-oxide has an action of bringing the construction of Th2 predominant immunocompetent cells back to normal. It was also confirmed that, since the production level of IFN-γ of the spleen cells of the mice applied with adenosine N1-oxide (Experiment group 2) decreased compared to the mice applied with the gel which had been prepared by adding refined water (Experiment group 1), adenosine N1-oxide has also an action of inhibiting the production of inflammatory cytokines produced by Th1 cells. Accordingly, the inhibition of atopic inflammation in the skin by the application of adenosine N1-oxide is judged to be exerted by these mechanisms in combination.

Experiment 17

<Influence of Adenosine N1-Oxide on Inflammatory Reaction of Keratinocyte>

Since adenosine N1-oxide was confirmed to have a therapeutic effect on atopic dermatitis in Experiment 11, the influence of adenosine N1-oxide on the inflammatory reaction of epidermal cells was examined in this experiment. When received stimulations such as ultraviolet rays, epidermal cells produce inflammatory cytokines such as TNF-α and IL-1 to induce inflammation in the skin, resulting in inducing or exacerbating skin troubles such as spots and wrinkles. Therefore, the influence of adenosine N1-oxide on the production of inflammatory cytokines when stimulated with ultraviolet rays was examined by using a human normal keratinocyte widely used as a human skin model.

Experiment Method 1

"CELLMATRIX TYPE IV", a product name of collagen for tissue culture commercialized by Nitta Gelatin Inc., Osaka, Japan, which had been diluted with PBS(K-) by 10 times, was previously placed in "FALCON 35-3001", a product name of 35 mm petri dish commercialized by Becton Dickinson and Company, NJ, USA, in an amount of 1 mL/plate, and then allowed to stand at ambient temperature for 10 min, followed by removing an excessive amount of CELLMATRIX, drying the petri dish in air, and washing it thrice with PBS(K-). "NHEK", a cell name of normal human epidermal keratinocyte, commercialized by Kurabo Industries Ltd., Osaka, Japan (called "NHEK cells", hereinafter), which had been suspended in "EPILIFE", a product name of basal medium for epidermal keratinocyte/corneal epithelial cells, commercialized by Kurabo Industries Ltd., Osaka, Japan (called "EpiLife medium", hereinafter), containing "EDGS", a product name of additive for proliferating normal human epidermal keratinocyte, commercialized by Kurabo Industries Ltd., Osaka, Japan, with final concentrations of 30 µg/mL of calf serum albumin, 5 µg/mL of transferrin derived from calf, 11 ng/mL of hydrocortisone, 10 ng/mL of human recombinant insulin-like factor type I, 1 ng/mL of a human recombinant epidermal growth factor, and 18 ng/mL of prostaglandin E2 (called "EDGS", hereinafter) at a cell concentration of $5 \times 10^4$ cells/1.5 mL/petri dish. The cells were cultured at 37° C. in a 5% v/v $CO_2$ incubator. On the $2^{nd}$ and $4^{th}$ days after the cell inoculation, the medium was replaced with EpiLife medium free of EDGS (1 mL/plate). On the $5^{th}$ day after the cell inoculation, the supernatant was removed, and the petri dish was washed twice by adding 1 mL/petri dish of Hanks' balanced salt solution (called "HBSS (−) buffer", hereinafter). Further, 2 mL/petri dish of HBSS (−) buffer was added to the petri dish which was then placed in the position 15 cm apart from an ultraviolet ray light source and irradiated with 40 mJ/cm$^2$ of ultraviolet B radiation. After the irradiation, HBSS (−) buffer was promptly removed and adenosine N1-oxide, which had been dissolved in EpiLife medium free of EDGS to give the concentrations shown in Table 20, was added to the petri dish in an amount of 1.5 mL/petri dish, followed by incubating the cells in a 5% v/v $CO_2$ incubator at 37° C. The supernatant was sampled at four- and six-hours after the addition of the medium containing adenosine N1-oxide, wherein the supernatant at four hours after the addition of the medium was assayed for cytotoxicity with an index of extracellularly released lactase dehydrogenase (called "LDH", hereinafter) with "Cell Cytotoxicity Assay Kit (LDH)", a product name of cytotoxicity assay kit commercialized by Roche Diagnostics K.K., Tokyo, Japan; and the supernatant at six hours after the addition of the medium was assayed for the levels of TNF-α, IL-1α, and IL-8 as inflammatory cytokines with ELISA. The results are in Table 20. As a control, cells were irradiated with ultraviolet B radiation (UVB) and assayed for cytotoxicity and production levels of cytokines similarly as above except for incubating the cells in EpiLife medium free of adenosine N1-oxide and EDGS. As an ultraviolet ray light source, "NS-8F", a light source for actual use commercialized by Sanwa Medical Co., Ltd., Okayama, Japan, equipped with an ultraviolet B radiation lamp was used, and the radiation dose was measured on "UVR-305/365D (II)", an ultraviolet ray meter commercialized by Topcon Corporation, Tokyo, Japan. TNF-α was assayed by the same method as in Experiment 2. The remaining other cytokines were assayed with an IL-1α assay kit, commercialized by R & D Systems Inc., MN, USA, and an IL-8 assay kit commercialized by BioLegend, CA, USA.

mation by adenosine N1-oxide is the inhibition of inflammatory cytokines produced from epidermal cells by the stimulation of ultraviolet rays. Unlike adenosine and inosine, adenosine N1-oxide inhibited LDH released from NHEK cells by the stimulation of ultraviolet rays in a dose-dependent manner, revealing that it has also an action of protecting cells from the cytotoxicity per see caused by ultraviolet rays. Although NHEK cells were inhibited proliferation by the stimulation of ultraviolet rays, no influence of the addition of adenosine N1-oxide, adenosine or inosine on the cell proliferation was observed.

Experiment 18

<Influence of Adenosine N1-Oxide on Oxidant Stress Against Fibroblasts>

Since Experiment 17 revealed that adenosine N1-oxide decreases the cytotoxicity by ultraviolet rays against epidermal cells in the skin and inhibits the production of inflammatory cytokines, a test for examining the influence of adenosine N1-oxide on the cytotoxicity against fibroblasts, whose inflammatory reaction is influenced by ultraviolet rays, was carried out in this experiment. Cells irradiated with ultraviolet rays are deemed to generate excessive amounts of free radicals to give oxidant stress on cells around the irradiated cells and to more enhance inflammatory reaction, and thus hydrogen oxide was used as an oxidant stress that imparts disorder to cells.

Experiment Method

Normal human fibroblasts (called "NHDF cells", hereinafter), which had been prepared with D-MEM medium supplemented with 10% fetal calf serum (FCS) into a cell suspension with a cell concentration of $6 \times 10^4$ cells/mL, was added to 96-well microplates commercialized by Becton, Dickinson and Company, CA, USA, in an amount of 100

TABLE 20

| Experiment group | Stimulation by ultra-violet rays | Concentration of ANO (μM) | Concentration of AN (μM) | Concentration of IN (μM) | TNF-α (pg/mL) | IL-α (pg/mL) | IL-8 (pg/mL) | LDH Activity (absorbance) | Proliferation (Fluorescent intensity) |
|---|---|---|---|---|---|---|---|---|---|
| 1 | No | 0 | 0 | 0 | 0 | 53 | 1 | 0.19 | 10170 |
| 2 | Yes | 0 | 0 | 0 | 141 | 246 | 169 | 0.36 | 5799 |
| 3 |  | 1 | 0 | 0 | 119 | 203 | 107 | 0.32 | 5540 |
| 4 |  | 5 | 0 | 0 | 76 | 173 | 89 | 0.23 | 5607 |
| 5 |  | 10 | 0 | 0 | 76 | 140 | 51 | 0.14 | 5682 |
| 6 |  | 0 | 1 | 0 | 144 | 243 | 177 | 0.35 | 5701 |
| 7 |  | 0 | 5 | 0 | 138 | 244 | 172 | 0.36 | 5683 |
| 8 |  | 0 | 10 | 0 | 138 | 239 | 175 | 0.35 | 5578 |
| 9 |  | 0 | 0 | 1 | 141 | 246 | 166 | 0.34 | 5643 |
| 10 |  | 0 | 0 | 5 | 142 | 243 | 169 | 0.34 | 5611 |
| 11 |  | 0 | 0 | 10 | 128 | 228 | 140 | 0.32 | 5633 |

ANO: Adenosine N1-oxide
AN: Adenosine
IN: Inosine

As evident from Table 20, adenosine N1-oxide inhibited the production of TNF-α and IL-8 from NHEK cells induced by ultraviolet rays in a dose-dependent manner. Also, adenosine N1-oxide inhibited the production of IL-1α from NHEK cells, augmented by ultraviolet rays (Experiment groups 3 to 5), in a dose-dependent manner. On the contrary, adenosine and inosine did not influence on the production of these cytokines from NHEK cells, induced or augmented by ultraviolet rays, at the concentrations used in this experiment (Experiment groups 6 to 10). These results indicate that one of the mechanisms of the inhibitory action on the skin inflam- μL/well, followed by incubating the cells at 37° C. for 72 hours in a $CO_2$ incubator. After the culture, hydrogen peroxide, which had been diluted with Hanks' solution (commercialized by Wako Pure Chemical Industries Ltd., Tokyo, Japan) to give a concentration of 400 μM, was added to the microplates in an amount of 100 μL/well (a final concentration of hydrogen peroxide: 200 μM), followed by incubating the cells at 37° C. for two hours. To the wells, which had not been treated with hydrogen peroxide, was added 100 μL/well of Hanks' solution. After the culture, all the supernatant in each well was removed by sucking, and adenosine N1-oxide, which had been diluted with D-MEM medium supplemented with 10% FCS to give the final concentrations shown in Table 21, was added to the wells in an amount of 100 μL/well, followed by culturing the cells for 24 hours. Thereafter, the supernatant in each well was removed by sucking, and "CELL COUNTING KIT-8", a product name of a reagent solution for counting viable cells, commercialized by Dojindo Molecular Technologies, Inc., Kumamoto, Japan, which had been diluted with D-MEM medium supplemented with 10% FCS by 20-times, was added to the wells in an amount of 100 μL/well, followed by incubating the cells in a 5% v/v $CO_2$ incubator at 37° C. for two hours. Finally, the microplates were measured for absorbance at a wavelength of 450 nm on a plate reader. For each well, a relative absorption value was determined when the absorbance of a well of NHDF cells, which had been cultured by the addition of only medium, was regarded as 100, and it is expressed as a cell survival rate (%) in Table 21.

TABLE 21

| Experiment group | Concentration of ANO (μM) | Addition of hydrogen peroxide | Cell survival rate (%) |
|---|---|---|---|
| 1 | 0 | No | 100 |
| 2 | 0 | Yes | 30 |
| 3 | 3.1 | Yes | 35 |
| 4 | 6.3 | Yes | 81 |
| 5 | 12.5 | Yes | 83 |
| 6 | 25.0 | Yes | 89 |
| 7 | 3.12 | No | 100 |
| 8 | 6.25 | No | 100 |
| 9 | 12.5 | No | 100 |
| 10 | 25.0 | No | 100 |

ANO: Adenosine N1-oxide

As evident from Table 21, NHDF cells were received cytotoxicity by the addition of hydrogen peroxide (Experiment group 2) and the cell survival rate decreased down to 30% compared to the case with no addition thereof (Experiment group 1). For the cells, which had been cultured in the medium containing adenosine N1-oxide after the addition of hydrogen peroxide (Experiment groups 3 to 6), the cell survival rate increased in a concentration-dependent manner of adenosine N1-oxide, and the cell survival rate was recovered up to 89% at a concentration of 25 μM. No influence of adenosine N1-oxide on the cell survival rate was observed at the concentrations used in this experiment (Experiment groups 7 to 10). The results indicate that adenosine N1-oxide has an action of protecting cells from oxidant stress generated accompanied by inflammation, and thus it can be useful as a prophylactic or therapeutic agent for skin inflammation induced by ultraviolet rays, as well as a prophylactic or therapeutic agent for diseases caused by exacerbation of vascular system's inflammatory reaction such as cardiac infarct and brain infarct.

Experiment 19

<Influence of Nucleic Acid and Derivatives Thereof on the Production of Inflammatory Cytokines by Macrophage>

Experiments 1 to 18 revealed that adenosine N1-oxide has a more improved anti-inflammatory action compared to adenosine and inosine, and one of the mechanisms of such is the inhibition of the production of inflammatory cytokines including TNF-α from cells in inflamed area. Therefore, the strength of inhibitory action of derivatives of adenine on the production of inflammatory cytokines was examined in this experiment. For comparison, the influence of glycyrrhizins, which are widely used as anti-inflammatory ingredients for quasi-drugs, on the production of inflammatory cytokines was examined.

<Test Method and Test Sample>

By using mouse macrophages prepared by the same method as in Experiment 2, they were cultured in a 5% v/v $CO_2$ incubator at 37° C. for 20 hours in the coexistence of 2 μg/mL of LPS and 10 IU/mL of IFN-γ similarly as in Experiment 2 and with the addition of 50 μL/well of a derivative of nucleic acid such as adenosines including adenosine N1-oxide, adenine, adenosine, 3'-α-glucosyl-adenosine N1-oxide, 5'-α-glucosyl-adenosine N1-oxide, adenosine N1-oxide 5'-monophosphate (CAS No. 4061-78-3), adenosine, adenosine 5'-monophosphate, adenine N1-oxide (commercialzied by MP Biomedicals, LLC, CA, USA), and inosine; and guanines including guanine, guanosine, guanosine 5'-monophosphate, 8-OH-deoxyguanine, and 8-OH-guanosine, all of which had been diluted with PBS to give a final concentration of 0.05 to 200 μM. IB-MECA (1-deoxy-1-[6-[[(3-iodophenyl-)methyl]amino]-9H-purin-9-yl]-N-methyl-3-β-ribofuranuronamide, commercialized by Sigma-Aldrich Corporation, St. Louis, Mo. USA), whose clinical exploitations had been in progress, and dipotassium glycyrrhizinate and 18β-glycyrrhetinate used as glycyrrhizins, which had been widely used as anti-inflammatory ingredients for quasi-drugs, were diluted with RPMI 1640 medium supplemented with 10% FCS to give a final concentration of 0.05 to 200 μM, followed by adding the dilutions to the wells in an amount of 50 μL/well and incubating the cells in a 5% v/v $CO_2$ incubator at 37° C. for 20 hours. After completion of the culture, the supernatant in each well was collected and assayed for cytokines and prostaglandin E2 (called "PGE2", hereinafter) with ELISA. Based on the data, the concentration of each of the nucleic acid derivatives or anti-inflammatory agents that inhibits the production of each cytokine by 50%, when the cells are cultured in the presence of LPS and mouse IFN-γ but without adding any nucleic acid derivative (called "$IC_{50}$ concentration", hereinafter), was determined and the results are in Table 22. The concentrations of nucleic acid derivatives used in determining $IC_{50}$ were adopted from those wherein the survival rates were not below 90% when the cell survival rate was regarded as 100% when the cells were cultured without adding any nucleic acid derivatives. The results are in Table 22.

TABLE 22

| Experiment group | Name of substances used in experiment | $IC_{50}$ Concentration (μM) | | | |
|---|---|---|---|---|---|
| | | TNF-α | IL-6 | PGE2 | IL-12 |
| 1 | ANO | 0.3 | 0.9 | 1.2 | 1.4 |
| 2 | Adenine | 85.2 | 200< | NT | NT |
| 3 | Adenosine | 17.4 | 50.1 | 200< | 14 |
| 4 | 3'-α-Glucosyl-adenosine N1-oxide | 0.8 | 3.2 | 2.8 | 5.2 |
| 5 | 5'-α-Glucosyl-adenosine N1-oxide | 10.8 | 38.3 | NT | NT |
| 6 | Adenosine N1-oxide 5'-monophosphate | 0.9 | 10.2 | NT | 200< |
| 7 | Adenosine 5'-monophosphate | 32.1 | Not inhibited | NT | NT |
| 8 | Adenine N1-oxide | 137.3 | 200< | NT | NT |
| 9 | Inosine | 200< | Enhanced | 200< | 200< |
| 10 | Guanine | Not inhibited | Not inhibited | NT | NT |
| 11 | Guanosine | Not inhibited | Not inhibited | NT | NT |

TABLE 22-continued

| Experiment group | Name of substances used in experiment | IC$_{50}$ Concentration (µM) | | | |
|---|---|---|---|---|---|
| | | TNF-α | IL-6 | PGE2 | IL-12 |
| 12 | Guanosine 5'-monophosphate | Not inhibited | Not inhibited | NT | NT |
| 13 | 8-OH-Deoxyguanine | 200< | Enhanced | NT | NT |
| 14 | 8-OH-Guanosine | 200< | Enhanced | NT | NT |
| 15 | IB-MECA | 0.4 | Not inhibited | NT | 4.5 |
| 16 | Dipotassium glycyrrhizinate | 200< | 200< | 200< | 200< |
| 17 | 18β-Glycyrrhetinate | 50.2 | 87.3 | 200< | 200< |

ANO: Adenosine N1-oxide
IB-MECA: 1-Deoxy-1-[6-[[(3-iodophenyl-)methyl]amino]-9H-purin-9-yl]-N-methyl-β-D-ribofuranuronamide
NT: Not tested As evident from Table 22, referring to the inhibition of the production of TNF-α from mouse intraperitoneal macrophages, which had been stimulated with LPS and IFN-γ, adenosine N1-oxide and IB-MECA showed IC$_{50}$ at the lowest concentrations among the nucleic acid derivatives used in this experiment, and next to them 3'-α-glucosyl-adenosine N1-oxide and adenosine N1-oxide 5'-monophosphate showed a strong inhibitory effect on the production of TNF-α. Adenine derivatives and guanines other than the above only exhibited a weak inhibition on the production of TNF-α. Adenosine N1-oxide, 3'-α-glucosyl-adenosine N1-oxide, and adenosine N1-oxide 5'-monophosphate also strongly inhibited the production of IL-6, but no inhibition on the production of IL-6 by IB-MECA was observed. Adenosine N1-oxide and 3'-α-glucosyl-adenosine N1-oxide showed an inhibitory action on the production of PGE2 and IL-12 as inflammatory mediators. The results indicate that adenosine N1-oxide, 3'-α-glucosyl-adenosine N1-oxide, and adenosine N1-oxide 5'-monophosphate are useful as a prophylactic and therapeutic agent for inflammatory diseases, and adenosine N1-oxide is more preferable. Among adenines, adenine, adenosine, adenosine 5'-monophosphate, and adenine N1-oxide have only a weak inhibitory action on the production of inflammatory cytokines, indicating that there exists a strong anti-inflammatory action in the part of adenosine N1-oxide. The reason why 5'-α-glucosyl-adenosine N1-oxide has a weaker function effect than 3'-α-glucosyl-adenosine N1-oxide can be speculated that the former is not susceptible to the action of glucosidase that hydrolyzes α-glucosyl adenosine N1-oxide into adenosine N1-oxide and glucose.

Experiment 20

<Acute Toxicity Test>

Two grams of adenosine N1-oxide, two grams of 3'-α-glucosyl-adenosine N1-oxide, or two grams of adenosine N1-oxide 5'-monophosphate was dissolved in 100 mL of PBS, followed by intraperitoneally administering each of the solutions to 10 BALB/c mice (6-week-old, female, average weight of 20 g, commercialized by Charles River Laboratories Japan Inc., Tokyo, Japan) at a dose of 1 mL/head and observing the following course of the mice for 24 hours. As a control, only PBS was intraperitoneally administered to 10 BALB/c mice (6-week-old, female, average weight of 20 g, commercialized by Charles River Laboratories Japan Inc., Tokyo, Japan) at a dose of 1 mL/head, followed by observing the course of the mice for 24 hours. At 24 hours after administering adenosine N1-oxide, 3'-α-glucosyl-adenosine N1-oxide, adenosine N1-oxide 5'-monophosphate, or PBS, the mice were sampled blood and urine for clinical assays that provide indices of renal and liver functions. Any of the mice administered with adenosine N1-oxide or derivatives thereof showed no change in appearance from just after the administrations through the completion of observations, and no difference was found in the clinical laboratory test results that provide indices of renal and liver functions between the test and control mice. The results indicate that the LD$_{50}$ of adenosine N1-oxide or derivatives thereof is 1,000 mg/kg body weight or more and is high in safeness even when administered to humans. Since the solubility of adenosine N1-oxide in PBS is about 20 mg/mL, the administration test at a dose of 1,000 mg/kg body weight or more was not conducted because the volume of the solution to be administered to a mouse at such a dose exceeds 1 mL, which is too much to be administered, becomes overloaded with the mouse.

The present invention is explained with reference to the following Examples but should never be restricted thereby. Incidentally, adenosine N1-oxide (with a purity of adenosine N1-oxide of about 99.5%, pyrogen free), which had been prepared at Hayashibara Biochemical Laboratories, Inc., Okayama, Japan, in accordance with the method in Experiment 1, was used.

Example 1

Agent for Injection

Three and half grams of adenosine N1-oxide was dissolved in an adequate amount of refined water for injection. In the adenosine N1-oxide solution were dissolved 0.1 g of calcium chloride, 0.15 g of potassium chloride, 3.0 g of sodium chloride, 1.55 g of sodium lactate, and 25 g of α,α-trehalose, and the solution was volumed up to 500 mL in total by adding water for injection. The resulting solution was sterilized by filtering, injected into plastic bags by 100 mL, and sealed to obtain a therapeutic agent for inflammatory diseases for a pyrogen-free injection. The product can be used as a prophylactic or therapeutic agent for inflammatory diseases such as sepsis, chronic rheumatism, ARDS, hepatitis, and inflammatory bowel disease. The product can be also used as a production inhibitor for TNF-α, IL-6, and IL-12, or a production enhancer for IL-10.

The stability of the agent for injection prepared in the above was evaluated. As a control, a specimen was prepared for use similarly as in the above, except for using 3.5 g of adenosine in place of the adenosine N1-oxide. The preparation prepared in the above was dissolved by using D-MEM medium free of human serum (Experiment group 1) or D-MEM medium supplemented with 10% v/v human serum (Experiment group 2) to give an adenosine N1-oxide concentration of 100 µM, and incubated at 37° C. for 7 or 24 hours. After completion of the incubation, the contents of adenosine N1-oxide remained in both of the media were determined for peak areas based on HPLC conducted under the following conditions and determined for relative values (%) when the peak area of adenosine N1-oxide just after being diluted with a medium free of serum (time 0) was regarded as 100. The results are shown in Table 23 as the residual percentages of adenosine N1-oxide. The control specimen was similarly dissolved by using D-MEM medium free from human serum (Experiment group 3) or D-MEM medium supplemented with 10% v/v human serum (Experiment group 4) to give an adenosine N1-oxide concentration of 100 µM, and the solution was incubated at 37° C. for 24 hours. After completion of the incubation, the residual adenosine present in the medium was quantitated on HPLC under the following conditions.

The residual percentage of adenosine N1-oxide or adenosine were determined based on their elution peak areas on HPLC, expressed with relative values (%), when the peak area of adenosine just after being diluted with a medium free of serum (time 0) was regarded as 100, and shown in Table 23 in parallel. For adenosine, the medium was sampled at 7 hours after initiating the incubation and determined for adenosine contained therein. The results are in Table 23 in parallel.

<HPLC Conditions>
HLPC Apparatus: SHIMADZU UV-VIS DETECTOR SPD-10AV
LC-10AT (Pump)
C-R8A (Recorder)
SIL-20AC (Autosampler)
Column for analysis: ODS Column (a product name: "YMC-PACK ODS-A", 4.6×250 mm, commercialized by YMC Co., Ltd., Kyoto, Japan)
Moving phase: (0.1% aqueous acetic acid solution):(methanol)=96:4
Detection sensitivity (AUFS): 0.01
Detection wavelength: 260 nm
Flow rate: 1 mL/min
Injection amount of sample for assay: 20 μL
Column temperature: 40° C.

TABLE 23

| Experiment group | Substance added to medium | Medium with or without human serum | Residual percentage (%) Incubation time | | |
|---|---|---|---|---|---|
| | | | 0 | 7 | 24 |
| 1 | ANO | Without | 100 | 100 | 100 |
| 2 | ANO | With | 100 | 100 | 100 |
| 3 | AN | Without | 100 | 100 | 100 |
| 4 | AN | With | 100 | 0 | 0 |

ANO: Adenosine N1-oxide
AN: Adenosine

As evident from Table 23, adenosine (AN) and adenosine N-oxide (ANO) remained 100% after 24-hours' incubation in the absence of human serum (Experiment groups 1 and 3). In contrast, adenosine was completely diminished after 7 hours' incubation in the presence of human serum (Experiment group 4), and adenosine N1-oxide remained 100% even after 24 hours' incubation in the presence of human serum (Experiment group 2). The results indicate that, unlike adenosine that is promptly degraded in human blood (see, for example, "The European Journal of Pharmacology", Vol. 93, page 21, 1983), adenosine N1-oxide, when administered to humans, is hardly degraded even in the serum and is capable of exerting effects as a therapeutic agent for inflammatory diseases for a relatively long period of time.

Example 2

Agent for Injection

Two grams of any one of adenosine N1-oxide, 3'-α-glucosyl-adenosine N1-oxide, and adenosine N1-oxide 5'-monophosphate was dissolved in 100 mL of PBS. Each of the resulting solutions was sterilized by filtering, injected into a glass vial by five milliliters, powdered by freeze-drying, and sealed to obtain a therapeutic agent for inflammatory diseases used for pyrogen-free injection in the form of a solid preparation to be reconstituted upon use. These products can be used as a prophylactic or therapeutic agent for inflammatory diseases such as sepsis, chronic rheumatism, ARDS, hepatitis, and inflammatory bowel disease. They can be also used as a production inhibitor for TNF-α, IL-6, and IL-12, or used as a production enhancer for IL-10.

The safeness of the preparations prepared in the above was evaluated. To each of the preparations prepared in the above was added five milliliters of refined water for injection, and each of the resulting solutions was intravenously administered to 10 BALB/c mice, 9-week-old, female, commercialized by Charles River Laboratories Japan Inc., Tokyo, Japan, at a dose of 0.3 mL/head once a day every day for successive seven days. For two weeks after initiating the administration, the mice were weighed every day and followed the course thereof, revealing that they showed no significant change in body weight and other appearance, compared to 10 BALB/c mice administered intravenously with PBS at a dose of 0.3 mL/head once a day every day for successive seven days. At two weeks after initiating the administrations, the mice were collected blood and urine and measured for clinical laboratory test results that provide indices of renal and liver functions, revealing that there exists no difference compared to those administered with only PBS. The results indicate that any of the preparations containing adenosine N1-oxide, 3'-α-glucosyl-adenosine N1-oxide, or adenosine N1-oxide 5'-monophosphate is high in safeness even when administered to humans.

Example 3

Agent for Injection

Two grams of any one of adenosine N1-oxide, 3'-α-glucosyl-adenosine N1-oxide, and adenosine N1-oxide 5'-monophosphate was dissolved in 100 mL of physiological saline for injection, and the resulting solutions were sterilized by filtering and powdered by freeze-drying. Each of the resulting powders was placed in an upper room of a plastic vessel having another lower room injected with 100 mL of refined water to obtain a pyrogen-free therapeutic agent for inflammatory diseases. These products can be used as a prophylactic or therapeutic agent for inflammatory diseases such as sepsis, chronic rheumatism, ARDS, hepatitis, and inflammatory bowel disease. They can be also used as a production inhibitor for TNF-α, IL-6, and IL-12, or used as a production enhancer for IL-10.

The preparations prepared in the above were respectively evaluated for the presence or absence of hemolyzing property. Blood, which had been collected from the heart of a BALB/c mouse in the presence of heparin, was washed thrice with PBS and suspended in PBS into a $5 \times 10^{10}$ cells/mL of erythrocyte suspension. The erythrocyte suspension and any of the above preparations which had been dissolved in the physiological saline placed in the lower room, were mixed in an equal amount, treated at 37° C. for 30 min, and centrifuged, followed by measuring the absorbance of the resulting supernatants at a wavelength of 580 nm. A fresh preparation of the same erythrocyte suspension as above and physiological saline for injection were mixed in an equal amount, treated at 37° C. for 30 min, and centrifuged, followed by measuring the absorbance of the resulting supernatant at a wavelength of 580 nm and comparing the absorbance with those obtained in the above. Since no difference was observed between them, it was judged that any of these preparations exhibit no action of erythrocyte hemolysis.

Example 4

Agent for Injection

In two grams of any one of adenosine N1-oxide, 3'-α-glucosyl-adenosine N1-oxide, and adenosine N1-oxide 5'-monophosphate, 0.02 g of calcium chloride, 0.03 g of potassium chloride, 0.6 g of sodium chloride, and 1 g of α,α-trehalose were dissolved in 85 mL of water for injection and volumed up to give a total volume of 100 mL. These solutions thus obtained were sterilized by filtering, injected into plastic bags, and sealed to obtain pyrogen-free therapeutic agents for inflammatory diseases. These products can be used as a prophylactic or therapeutic agent for inflammatory diseases such as sepsis, chronic rheumatism, ARDS, hepatitis, and inflammatory bowel disease. They can be also used as a production inhibitor for TNF-α, IL-6, and IL-12, or used as a production enhancer for IL-10.

Example 5

Agent for Injection

Two grams of any one of adenosine N1-oxide, 3'-α-glucosyl-adenosine N1-oxide, and adenosine N1-oxide 5'-monophosphate was dissolved in 100 mL of phosphate buffered saline. The solutions thus obtained were freeze-dried into powders after sterilization by filtering, and two milliliters of each of which was injected into a glass vial by two milliliters and sealed to obtain therapeutic agents for inflammatory diseases for injection in the form of a solid preparation to be reconstituted upon use. These products can be used as a prophylactic or therapeutic agent for inflammatory diseases such as sepsis, chronic rheumatism, ARDS, hepatitis, and inflammatory bowel disease. They can be also used as a production inhibitor for TNF-α, IL-6, and IL-12, or used as a production enhancer for IL-10.

Example 6

Oral Agent

Ten parts by weight of any one of adenosine N1-oxide, 3'-α-glucosyl-adenosine N1-oxide, and adenosine N1-oxide 5'-monophosphate, 90 parts by weight of α,α-trehalose, and 0.2 part by weight of magnesium stearate were mixed, and 0.5 g of each of which was tableted to prepare an oral therapeutic agent for inflammatory diseases. These products can be used as a prophylactic or therapeutic agent for inflammatory diseases such as sepsis, chronic rheumatism, ARDS, hepatitis, and inflammatory bowel disease. They can be also used as a production inhibitor for TNF-α, IL-6, and IL-12, or used as a production enhancer for IL-10.

Example 7

Oral Agent

One part by weight of any one of adenosine N1-oxide, 3'-α-glucosyl-adenosine N1-oxide, and adenosine N1-oxide 5'-monophosphate, 30 parts by weight of "FINETOSE", a product name of anhydrous crystalline maltose commercialized by Hayashibara Shoji, Inc., Okayama, Japan, and 0.4 part by weight of magnesium sulfate were mixed to homogeneity. 0.2 g of each of these mixtures was tableted in usual manner to prepare an oral therapeutic agent for inflammatory diseases. These products can be used as a prophylactic or therapeutic agent for inflammatory diseases such as sepsis, chronic rheumatism, ARDS, hepatitis, and inflammatory bowel disease. They can be also used as a production inhibitor for TNF-α, IL-6, and IL-12, or used as a production enhancer for IL-10.

Example 8

Powder

To 20 parts by weight of refined water were added one part by weight of any one of adenosine N1-oxide, 3'-α-glucosyl-adenosine N1-oxide, and adenosine N1-oxide 5'-monophosphate, two parts by weight of α-glucosyl hesperidin or α-glucosyl rutin, and one part by weight of cyclonigerosylnigerose (cyclic tetrasaccharide produced by Hayashibara Biochemical Laboratories, Inc., Okayama, Japan), followed by mixing them for dissolving and spray-drying the resulting solution in usual manner to obtain three types of anti-inflammatory therapeutic agents for inflammatory diseases. When orally taken alone or in a composition form with an orally intakable additive(s) for other food products, cosmetics, quasi-drugs, and/or pharmaceuticals, the above products can be used as a prophylactic or therapeutic agent for inflammatory diseases such as sepsis, chronic rheumatism, ARDS, hepatitis, and inflammatory bowel disease. They can be also used as a production inhibitor for TNF-α, IL-6, and IL-12, or used as a production enhancer for IL-10. The above products can be applied to the skin after dissolving in water or formulating into the form of an external dermal agent supplemented with an additive(s) for cosmetics and pharmaceuticals to improve atopic dermatitis and skin inflammation including dermatitis induced by suntan and to reduce melanin deposition in the skin.

<Composition 1: Example of Composition in the Form of a Cream for Treating Inflammatory Diseases>

| Ingredients | (% by weight) |
| --- | --- |
| (1) Propylene glycol | 5 |
| (2) Beeswax | 5 |
| (3) Cetyl alcohol | 4 |
| (4) Hydrogenated lanolin | 5 |
| (5) Squalane | 35 |
| (6) Stearic glyceride | 2 |
| (7) Polyoxyethylene (20 moles) sorbitan monolaurate | 2 |
| (8) Adenosine N1-oxide or 3'-α-glucosyl-adenosine N1-oxide | 1 |
| (9) Antiseptic | q.s. |
| (10) Flavor | q.s. |

Refined water in an amount sufficient for volume up to 100% by weight.

To confirm effectively of the agent for improving skin conditions containing adenosine N1-oxide, a test with volunteers was conducted by using the cream with the above composition. Forty females, 30- to 50-year-old, who had been troubled over chronic skin roughness, were selected as volunteers by diagnosis and randomly grouped into four groups, 10 subjects each. Ten volunteers in one group were allowed to apply the above cream (containing adenosine N1-oxide: Cream 1) to the part of rough skin thrice a day (morning, noon, and evening) every day for a month. Ten volunteers in another one group were allowed to apply the above cream (containing 3'-α-glucosyl-adenosine N1-oxide: Cream 2) to the part of rough skin thrice a day (morning, noon, and evening) every day for a month. Ten volunteers in another one group were allowed to apply a cream with the same composition as in the above (containing adenosine: Cream 3) except for replacing adenosine N1-oxide or 3'-α-glucosyl-adenosine N1-oxide with 1% by weight of adenosine to the part of rough skin thrice a day (morning, noon, and evening) every day for a month. The ten volunteers in the remaining one group were allowed to apply a cream with the same composition as in the above (Cream 4) except for excluding the agent for improving skin conditions of the present invention or adenosine thrice a day (morning, noon, and evening) every day for a month. The volunteers were measured for the moisture contents in their skin and evaluated the conditions of their wrinkles as a wrinkle score for judging their rough skin. In this method, it means that the moisture contents in their skin after applying the test samples were increased compared to those before applying them and the conditions of rough skin became more improved as the wrinkle score decreased.

<Assay for Moisture Content in the Skin>

On the previous day of applying any of the creams and the next day of completing the applications, the moisture content and the wrinkle score for the skin applied with the creams were determined. The moisture content in the skin was measured by using "SKICON-200EX", a product name of apparatus for measuring moisture content, commercialized by I.B.S Co., Ltd., Shizuoka, Japan, and the average value of the ten volunteers applied with each cream are in Table 24.

<Judgement Method for Wrinkle Score>

For each volunteer, the judgement of wrinkle score was macroscopically evaluated by five judges with criteria of the eight grades of wrinkle scores as shown in Table 25, based on a guideline of evaluation for the function of cosmetics (see, for example, "*Japanese Cosmetic Science Society*", Vol. 30, No. 4, pp. 316-332, 2006). The scores for each volunteer by the five judges were averaged for use as the wrinkle score for each volunteer and shown in Table 24 in parallel as the average value of the ten volunteers applied with each cream.

TABLE 24

| Test cream | | Moisture content in the skin (µS) | Wrinkle score |
|---|---|---|---|
| Cream 1 | Before application | 17 ± 4 | 2.18 |
| | After application | 29 ± 1* | 1.16* |
| Cream 2 | Before application | 17 ± 8 | 2.16 |
| | After application | 24 ± 1* | 1.46* |
| Cream 3 | Before application | 18 ± 2 | 2.11 |
| | After application | 19 ± 3 | 1.99 |
| Cream 4 | Before application | 17 ± 5 | 2.19 |
| | After application | 19 ± 5 | 2.12 |

There exists a significant difference compared to before applying cream (*$P < 0.05$).

TABLE 25

| Wrinkle score (grade) | Criterion of judgement |
|---|---|
| 0 | Free of wrinkle |
| 1 | Unclear shallow wrinkle is slightly observed |
| 2 | Clear shallow wrinkle is slightly observed |
| 3 | Clear shallow wrinkle is observed |
| 4 | Slightly deep wrinkle is slightly observed among clear shallow wrinkle |
| 5 | Slightly deep wrinkle is observed |
| 6 | Clear deep wrinkle is observed |
| 7 | Distinctly deep wrinkle is observed |

As evident from Table 24, when applied with the cream incorporated with adenosine N1-oxide (Cream 1) and the cream with 3'-α-glucosyl-adenosine N1-oxide (Cream 2), the moisture content in the skin and the wrinkle score were significantly improved compared to those before their applications. The cream incorporated with adenosine N1-oxide tended to be stronger in terms of the strength of improvement. On the contrary, the cream incorporated with adenosine in place of adenosine N1-oxide or 3'-α-glucosyl-adenosine N1-oxide (Cream 3), and the cream incorporated with no adenosine N1-oxide, 3'-α-glucosyl-adenosine N1-oxide, and adenosine (Cream 4) showed no significant improvement both in the moisture content in the skin and the wrinkle score even after the application compared to those before the application, and did not improve the volunteers' rough skin. Adenosine N1-oxide was judged to be superior in safeness because no abnormality inherent to the following creams was induced even during and after the test for applying the cream incorporated with adenosine N1-oxide (Cream 1) and the cream with 3'-α-glucosyl-adenosine N1-oxide (Cream 2).

By using the above creams, the influence on the inflammation and the melanin formation induced by suntan (ultraviolet rays) was evaluated.

<Volunteers>

Twenty volunteers, 22- to 45-year-old (10 males and 10 females), were intended. The volunteers were previously questioned and those whose skins are highly susceptible to suntan (become red) but not become colored and those whose skins are never suntanned (not become red) but become highly colored were omitted.

<Ultraviolet Rays Irradiating Apparatus>

Light Source ("NS-8F Model" Commercialized by Sanwa Medical Co., Ltd., Okayama, Japan)

Ultraviolet fluorescent lamp ("FL-20SE", commercialized by Toshiba Corporation, Tokyo, Japan), five pieces <Measurement for the Minimum Erythemogenic Dose>

A part in the inside of the right upper arm of each volunteer, which had been previously confirmed to have no spots and wounds and have roughly homogeneous skin color, was irradiated with a 25, 50, 75, 100, 125 or 150 mJ/cm$^2$ ultraviolet rays (UVB) at respective areas of 1×1 cm. At 24 hours after the irradiation, the irradiated parts were macroscopically observed and a dose at which stigmatism had been found was regarded as the minimum irradiation dose of ultraviolet rays for each volunteer.

<Measurement of the Degree of Inflammatory Reaction>

The following were recorded: The period of time until erythema in the ultraviolet-rays-irradiated part for each volunteer become to be unconfirmed by both visual contact and digital camera's image, and the period of time until pigmentation starts.

<Measurement for Melanin Index>

Melanin index was measured on "CM-700d", a spectrophotometer commercialized by Konica Minolta Holdings, Inc., Tokyo, Japan.

<Test Method>

In was confirmed that there were no spots and wounds in the inside of the left upper arm in each volunteer. On the day of initiating the test, four sites in the test part of each volunteer were irradiated with 1.5-times of the minimum erythemogenic dose of ultraviolet rays (UVB). The area of the irradiated site was in the range of 1×1 cm applied with each test sample. Just after the first UVB irradiation, each test part was applied with any of Creams 1 to 4 thrice a day (morning, noon, and evening) every day for 28 days at a dose of about 0.3 g/test sample/shot by taking each cream on a finger tip. In this case, care was taken not to mix one cream with any other creams. During the test period of time, care was taken not to wash the part applied with any of the creams for 30 min after the application. The part applied with any of the test samples and around the part were allowed not to be exposed to strong ultraviolet rays such as sunlight. The test was carried out in a double blind manner.
<Evaluation Method>

From the day of initiating the irradiation of ultraviolet rays until seven days after the initiation, the test parts were visually observed and photographed by a digital camera every day, and the day, on which the erythema in the part irradiated with ultraviolet rays become unobserved, was confirmed and the days until the unobserved day for each creams were averaged and shown in Table 26. At 24 hours after the irradiation of ultraviolet rays, the degree of erythema in the part applied with each cream was scored based on the three grades of "strong (2)", "no difference (0)", and "weak (−2)" compared to the part applied with Cream 3, summed up the scores for each cream, and averaged. The visual judgement of effect was conducted by five judges and the scores were averaged. The days, on which the erythema in the part irradiated with ultraviolet rays become unobserved, were averaged and shown in Table 26 in parallel. On 28 days after initiating the irradiation of ultraviolet rays, visual judgement on the part irradiated with ultraviolet rays and the melanin index were measured to confirm the degree of pigmentation. The averages of the results of the parts applied with each cream for the 20 volunteers are shown in Table 26 in parallel. The visual degree of pigmentation was scored based on the five grades of "apparently more (−2)", "slightly more (−1)", "no difference (0)", "slightly less (1)", and "apparently less (2)", summed up for each creams, and averaged. The visual judgement of effect was conducted by five judges and the scores were averaged. The melanin index was expressed by obtaining a relative value of the part applied with any of other creams when the measured value for Cream 4 was regarded as 100(%), and each data were averaged. The meaning of this experiment is as follows: The higher the score of visual judgement, the higher the pigmentation inhibitory effect (inhibition of melanin formation); and the lower the percentage (%) of melanin index, the higher the pigmentation inhibitory effect (inhibition of melanin formation).

TABLE 26

| Experiment group | Test cream | Ingredient incorporated into applied cream | Erythema Days until diminished | Erythema Degree | Pigmentation Degree | Pigmentation Index |
|---|---|---|---|---|---|---|
| 1 | Cream 1 | ANO | 21* | 1.3 | 1.2* | 56* |
| 2 | Cream 2 | 3'-G-ANO | 24* | 0.9 | 0.9* | 68* |
| 3 | Cream 3 | AN | 29 | 0.2 | 0.4 | 98 |
| 4 | Cream 4 | None | 30 | — | — | 100 |

ANO: Adenosine N1-oxide
3'-G-ANO: 3'-α-Glucosyl-adenosine N1-oxide
AN: Adenosine
There exists a significant difference against Experiment group 4 (*P < 0.05).

As shown in Table 26, the pigmentation of the part applied with the cream containing adenosine N1-oxide (Cream 1) and the cream incorporated with 3'-α-glucosyl-adenosine N1-oxide (Cream 2) were distinctly inhibited in both the visual score and the melanin index, compared to the part applied with the cream substrate containing none of the above compounds (Cream 4). In terms of the inhibitory strength, the cream incorporated with adenosine N1-oxide tended to be strong. The part applied with the cream containing adenosine (Cream 3) had no difference compared to the part applied with Cream 4 in the degree of pigmentation. This result and the above results of the moisture content and the wrinkle score indicate that adenosine N1-oxide and 3'-α-glucosyl-adenosine N1-oxide are superior in the action of improving the skin conditions. Combining this result with the results of the above experiments, such improvement effect of adenosine N1-oxide or 3'-α-glucosyl-adenosine N1-oxide on the skin conditions can be speculated to be the action of effectively inhibiting the skin inflammation induced by ageing, irradiation of ultraviolet rays, or the like. Adenosine N1-oxide and 3'-α-glucosyl-adenosine N1-oxide can be speculated to have no problem in safeness even when applied to the skin because they induced no red flare, eczema, etc., and there was found no problem in the volunteers' health conditions except for observing erythema and pigmentation induced by the irradiation of ultraviolet rays on the parts of the volunteers applied with the test samples.

<Example of Ingredient 2: Example of Composition of a Therapeutic Agent for Inflammatory Diseases of the Present Invention>

| Ingredient | (% by weight) |
|---|---|
| (1) Glycerin | 3 |
| (2) Propylene glycol | 4 |
| (3) Ethanol | 8 |
| (4) Polyoxyethylene (20 moles) olein alcohol | 0.5 |
| (5) Any one of adenosine N1-oxide, 3'-α-glucosyl-adenosine N1-oxide, and adenosine N1-oxide 5'-monophosphate; or | 1 |
| any one of the skin-improving agent of Examples 5 to 8 | 3 |
| (6) Indigo extract solution | 2 |
| (7) Citric acid | 0.01 |
| (8) Sodium citrate | 0.1 |
| (9) Flavor | 0.05 |

Refined water sufficient for volume up to 100% by weight.

The composition with the example of composition improves the inflammation in the skin and preferably maintains the skin conditions when used typically. The external dermal agent with the example of composition is also superior in skin-whitening effect.

<Ingredient 3: Example of Composition of an External Dermal Agent in the Form of a Pack of the Therapeutic Agent for Inflammatory Diseases of the Present Invention>

| Ingredient | (% by weight) |
|---|---|
| (1) Polyvinyl alcohol | 15 |
| (2) Polyethylene glycol | 3 |
| (3) Propylene glycol | 7 |
| (4) Ethanol | 10 |
| (5) Royal jelly extract | 1 |
| (6) Any one of adenosine N1-oxide, 3'-α-glucosyl-adenosine N1-oxide, and adenosine N1-oxide 5'-monophosphate | 0.5 |
| (7) Antiseptic | q.s. |
| (8) Flavor | q.s. |

Refined water sufficient for volume up to 100% by weight.

The composition with the example of ingredients improves the inflammation in the skin and preferably maintains the skin conditions when used typically. The external dermal agent with the example of ingredients is also superior in skin-whitening effect.

<Ingredient 4: Example of Composition of a Therapeutic Agent for Inflammatory Diseases of the Present Invention as an External Dermal Agent in the Form of a Dentifrice>

| Ingredient | (% by weight) |
|---|---|
| (1) Calcium carbonate | 50 |
| (2) Glycerin | 20 |
| (3) Carboxymethyl cellulose | 2 |
| (4) Sodium lauryl sulfate | 2 |
| (5) Any one of adenosine N1-oxide, 3'-α-glucosyl-adenosine N1-oxide, and adenosine N1-oxide 5'-monophosphate | 1 |
| (6) Saccharine | 0.1 |
| (7) Chlorhexidine | 0.01 |
| (8) Flavor | q.s. |

Refined water sufficient for volume up to 100% by weight.

The composition with the example of ingredients improves the gums' and oral inflammation induced by periodontal diseases or the like and preferably maintains the oral conditions when used typically. The external dermal agent with the above example of composition is also superior in gums' dullness-improving effect.

INDUSTRIAL APPLICABILITY

The therapeutic agent for inflammatory diseases containing adenosine N1-oxides as an effective ingredient of the present invention can be used as a prophylactic or therapeutic agent for inflammatory diseases including sepsis, hepatitis, inflammatory bowel disease, hemolytic-uremic syndrome, pancreatitis, nephritis, and dermatitis in the field of pharmaceuticals, food products, cosmetics, and quasi-drugs.

The invention claimed is:

1. A method for treating an inflammatory disease selected from the group consisting of sepsis, inflammatory bowel disease, pancreatitis, nephritis, gingivitis, and periodontal disease, comprising administering to a subject in need thereof one or more ingredients effective for treating the inflammatory disease and selected from the group consisting of adenosine N1-oxide corresponding to CAS No. 146-92-9, adenosine N1-oxide 5'-monophosphate, adenosine N1-oxide 5'-diphosphate, adenosine N1-oxide 5'-triphosphate, 3'-α-glucosyl-adenosine N1-oxide, and 5'-α-glucosyl-adenosine N1-oxide, to treat the inflammatory disease.

2. The method of claim 1, wherein said one or more effective ingredients is in the form of a tablet, ball, powder, liquid, suspension, emulsion, granule, or capsule in an amount of 1 to 90% by mass in terms of said adenosine N1-oxide.

3. The method of claim 1, wherein the only ingredients effective for treating the inflammatory disease that are administered to the subject are the one or more ingredients selected from the group consisting of adenosine N1-oxide, adenosine N1-oxide 5'-monophosphate, adenosine N1-oxide 5'-diphosphate, adenosine N1-oxide 5'-triphosphate, 3'-α-glucosyl-adenosine N1-oxide, and 5'-α-glucosyl-adenosine N1-oxide.

4. The method of claim 2, wherein the only ingredients effective for treating the inflammatory disease that are administered to the subject are the one or more ingredients selected from the group consisting of adenosine N1-oxide, adenosine N1-oxide 5'-monophosphate, adenosine N1-oxide 5'-diphosphate, adenosine N1-oxide 5'-triphosphate, 3'-α-glucosyl-adenosine N1-oxide, and 5'-α-glucosyl-adenosine N1-oxide.

* * * * *